(12) United States Patent
Jolidon et al.

(10) Patent No.: US 7,589,089 B2
(45) Date of Patent: Sep. 15, 2009

(54) INHIBITORS FOR GLYT-1

(75) Inventors: Synese Jolidon, Blauen (CH); Robert Narquizian, Saint Louis (FR); Emmanuel Pinard, Linsdorf (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 11/895,097

(22) Filed: Aug. 23, 2007

(65) Prior Publication Data
US 2008/0058331 A1 Mar. 6, 2008

(30) Foreign Application Priority Data
Aug. 30, 2006 (EP) .................... 06119758

(51) Int. Cl.
| | | |
|---|---|---|
| C07D 261/06 | (2006.01) | |
| C07D 307/02 | (2006.01) | |
| C07D 333/02 | (2006.01) | |
| C07D 333/50 | (2006.01) | |
| C07D 295/00 | (2006.01) | |
| C07D 213/02 | (2006.01) | |
| C07D 317/44 | (2006.01) | |
| A61K 31/5375 | (2006.01) | |
| A61K 31/164 | (2006.01) | |
| A61K 31/341 | (2006.01) | |
| A61K 31/357 | (2006.01) | |
| A61K 31/381 | (2006.01) | |
| A61K 31/42 | (2006.01) | |
| A61K 31/44 | (2006.01) | |
| C07C 233/00 | (2006.01) | |

(52) U.S. Cl. .................... 514/235.5; 514/355; 514/438; 514/443; 514/471; 514/616; 544/131; 546/316; 548/248; 549/76; 549/493; 564/155

(58) Field of Classification Search ........................ None
See application file for complete search history.

(56) References Cited

U.S. PATENT DOCUMENTS

| | | | | |
|---|---|---|---|---|
| 4,303,673 A * | 12/1981 | Biedermann et al. | ........ | 514/616 |
| 4,661,494 A * | 4/1987 | Spatz | .................... | 514/255.06 |
| 6,458,959 B1 * | 10/2002 | Crute et al. | .................. | 548/194 |
| 6,949,543 B2 * | 9/2005 | Kontani et al. | ........... | 514/230.5 |

FOREIGN PATENT DOCUMENTS

| | | |
|---|---|---|
| FR | 2 465 712 | 3/1981 |
| GB | 2 058 752 | 6/1980 |
| JP | 47-38426 | * 9/1972 |
| WO | WO 03/103651 | 12/2003 |
| WO | WO 2006/080477 | 8/2006 |

OTHER PUBLICATIONS

Yamazaki et al., Chemical Abstracts, 78:4517, 1973.*

CA Registry No. 875865-26-2, entry date in Registry file is Mar. 5, 2006.*
CA Registry No. 875465-23-9, entry date in Registry file is Feb. 28, 2006.*
CA Registry No. 851270-07-0, entry date in Registry file is May 27, 2005.*
CA Registry No. 851629-06-6, entry date in Registry file is Jun. 3, 2005.*
CA Registry No. 903353-13-9, entry date in Registry file is Aug. 22, 2006.*
CA Registry No. 850350-29-7, entry date in Registry file is May 12, 2005.*
CA Registry No. 850654-12-5, entry date in Registry file is May 18, 2005.*
English Translation of JP 47-38426, Sep. 28, 1972.*
Spatz et al., Tetrahedron Letters, 48(45), 8060-8064, 2007.*
Lewis D.A. & Lieberman J.A., Neuron. vol. 28, pp. 325-334 (2000).
Vandenberg R. J. & Aubrey K. R., Exp. Opin. Ther. Targets vol. 5(4) pp. 507-518 (2001).
Nakazato A. & Okuyama S., Exp. Opin. Ther. Patents vol. 10(1) pp. 75-98 (2000).

(Continued)

*Primary Examiner*—Fiona T Powers
(74) *Attorney, Agent, or Firm*—George W. Johnston; Patricia S. Rocha-Tramaloni; Kimberly J. Prior

(57) ABSTRACT

The present invention relates to compounds of formula I

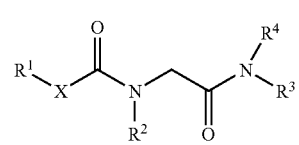

I wherein
$R^1$, $R^2$,
$R^3$,
$R^4$, and
X are as defined herein or to pharmaceutically acceptable acid addition salts thereof, with the exception of
4-methoxy-N-[2-oxo-2-(phenylamino)ethyl]-N-phenyl-benzamide,
4-chloro-N-[2-[(4-methylphenyl)amino]-2-oxoethyl]-N-phenyl-benzamide,
4-chloro-N-[2-[5-chloro-2-methoxyphenyl)amino]-2-oxoethyl]-N-benzamide,
4-methyl-N-(2-oxo-2-[(2,4,6-trichlorophenyl)amino]ethyl]-N-benzamide,
N-[2-[(4-methylphenyl)amino]-2-oxoethyl]-N-phenyl-benzamide,
4-methyl-N-[2-[(4-methylphenyl)amino]-2-oxoethyl]-N-phenyl-benzamide,
4-chloro-N-(2-oxo-2-[(2,4,6-trichlorophenyl)amino]ethyl]-N-benzamide and
N-[2-[(2,4-dimethoxyphenyl)amino]-2-oxoethyl]-N-[(2-fluorophenyl)methyl]-benzeneacetamide. The compounds are useful in the treatment of neurological and neuropsychiatric disorders.

8 Claims, No Drawings

OTHER PUBLICATIONS

Sharma T., Br. J. Psychiatry, vol. 174 (Suppl. 38) pp. 44-51 (1999).
Javitt D. C. et al., Biol. Psychiatry, vol. 45 pp. 668-679 (1999).
Mohn A. R., Cell vol. 98 pp. 427-436 (1999).
Bliss, T. V. & Collingridge G. L., Nature, vol. 361 pp. 31-39 (1993).
Tang J. P. et al., Nature, vol. 401, pp. 63-69 (1999).
Gainetdinov R. R. et al., Trends in Pharm. Sci. vol. 23(8) pp. 367-373 (2002).
Lopez-Corcuera B, et al., Mol. Mem. Biol. vol. 18 pp. 13-20 (2001).
Bergeron R. et al., Proc. Natl. Acad. Sci. USA vol. 95, pp. 15730-15734 (1998).
Chen et al., J. Neurophysiol. vol. 89(2) pp. 691-703 (2003).
Armer et al., Exp. Opin. Ther. Patents, vol. 11(4) pp. 563-572 (2001).
Pralong et al., Prog. Neurobiol. vol. 67 pp. 173-202 (2002).
Carlsson M. L., Neural, Trans. pp. 525-535 (1998).
Lindsley et al., Current Topics in Medicinal Chem. vol. 6, pp. 1883-1896 (2006).
Carrier et al., Bull. Soc. Chim. Fr vol. 130 pp. 405-416 (1993).
Potts et al., J. Org. Chem. vol. 36, No. 22 pp. 3368-3372 (1971).
Marraud et al., J. de Chimie Physique vol. 72 pp. 1173-1176 (1975).
Halberkann, J., Chemische Berichte vol. 54 pp. 1152-1167 (1921).
English language translation attached.
Boyd et al., J. of the Chemical Society, Perkin Transactions I, pp. 909-913 (1972).

* cited by examiner

INHIBITORS FOR GLYT-1

PRIORITY TO RELATED APPLICATION(S)

This application claims the benefit of European Patent Application No. 06119758.8, filed Aug. 30, 2006, which is hereby incorporated by reference in its entirety.

BACKGROUND OF THE INVENTION

Schizophrenia is a progressive and devastating neurological disease characterized by episodic positive symptoms such as delusions, hallucinations, thought disorders and psychosis and persistent negative symptoms such as flattened affect, impaired attention and social withdrawal, and cognitive impairments (Lewis D A and Lieberman J A, Neuron, 2000, 28:325-33). For decades research has focused on the "dopaminergic hyperactivity" hypothesis which has led to therapeutic interventions involving blockade of the dopaminergic system (Vandenberg R J and Aubrey K R., Exp. Opin. Ther. Targets, 2001, 5 (4): 507-518; Nakazato A and Okuyama S, et al., 2000, Exp. Opin. Ther. Patents, 10 (1): 75-98). This pharmacological approach poorly address negative and cognitive symptoms which are the best predictors of functional outcome (Sharma T., Br. J. Psychiatry, 1999, 174 (suppl. 28): 44-51).

A complementary model of schizophrenia was proposed in the mid-1960' based upon the psychotomimetic action caused by the blockade of the glutamate system by compounds like phencyclidine (PCP) and related agents (ketamine) which are non-competitive NMDA receptor antagonists. Interestingly in healthy volunteers, PCP-induced psychotomimetic action incorporates positive and negative symptoms as well as cognitive dysfunction, thus closely resembling schizophrenia in patients (Javitt D C et al., 1999, Biol. Psychiatry, 45: 668-679 and refs. herein). Furthermore transgenic mice expressing reduced levels of the NMDAR1 subunit displays behavioral abnormalities similar to those observed in pharmacologically induced models of schizophrenia, supporting a model in which reduced NMDA receptor activity results in schizophrenia-like behavior (Mohn A R et al., 1999, Cell, 98: 427-236).

Glutamate neurotransmission, in particular NMDA receptor activity, plays a critical role in synaptic plasticity, learning and memory, such as the NMDA receptors appears to serve as a graded switch for gating the threshold of synaptic plasticity and memory formation (Hebb DO, 1949, The organization of behavior, Wiley, N.Y.; Bliss T V and Collingridge GL, 1993, Nature, 361: 31-39). Transgenic mice overexpressing the NMDA NR2B subunit exhibit enhanced synaptic plasticity and superior ability in learning and memory (Tang J P et al., 1999, Nature: 401-63-69).

Thus, if a glutamate deficit is implicate in the pathophysiology of schizophrenia, enhancing glutamate transmission, in particular via NMDA receptor activation, would be predicted to produce both anti-psychotic and cognitive enhancing effects.

The amino acid glycine is known to have at least two important functions in the CNS. It acts as an inhibitory amino acid, binding to strychnine sensitive glycine receptors, and it also influences excitatory activity, acting as an essential co-agonist with glutamate for N-methyl-D-aspartate (NMDA) receptor function. While glutamate is released in an activity-dependent manner from synaptic terminals, glycine is apparently present at a more constant level and seems to modulate/control the receptor for its response to glutamate.

One of the most effective ways to control synaptic concentrations of neurotransmitter is to influence their re-uptake at the synapses. Neurotransmitter transporters by removing neurotransmitters from the extracellular space, can control their extracellular lifetime and thereby modulate the magnitude of the synaptic transmission (Gainetdinov R R et al, 2002, Trends in Pharm. Sci., 23 (8): 367-373).

Glycine transporters, which form part of the sodium and chloride family of neurotransmitter transporters, play an important role in the termination of post-synaptic glycinergic actions and maintenance of low extracellular glycine concentration by re-uptake of glycine into presynaptic nerve terminals and surrounding fine glial processes.

Two distinct glycine transporter genes have been cloned (GlyT-1 and GlyT-2) from mammalian brain, which give rise to two transporters with ~50% amino acid sequence homology. GlyT-1 presents four isoforms arising from alternative splicing and alternative promoter usage (1a, 1b, 1c and 1d). Only two of these isoforms have been found in rodent brain (GlyT-1a and GlyT-1b). GlyT-2 also presents some degree of heterogeneity. Two GlyT-2 isoforms (2a and 2b) have been identified in rodent brains. GlyT-1 is known to be located in CNS and in peripheral tissues, whereas GlyT-2 is specific to the CNS. GlyT-1 has a predominantly glial distribution and is found not only in areas corresponding to strychnine sensitive glycine receptors but also outside these areas, where it has been postulated to be involved in modulation of NMDA receptor function (Lopez-Corcuera B et al., 2001, Mol. Mem. Biol., 18: 13-20). Thus, one strategy to enhance NMDA receptor activity is to elevate the glycine concentration in the local microenvironment of synaptic NMDA receptors by inhibition of GlyT-1 transporter (Bergereon R. Et al., 1998, Proc. Natl. Acad. Sci. USA, 95: 15730-15734; Chen L et al., 2003, J. Neurophysiol., 89 (2): 691-703).

Glycine transporters inhibitors are suitable for the treatment of neurological and neuropsychiatric disorders. The majority of diseases states implicated are psychoses, schizophrenia (Armer R E and Miller D J, 2001, Exp. Opin. Ther. Patents, 11 (4): 563-572), psychotic mood disorders such as severe major depressive disorder, mood disorders associated with psychotic disorders such as acute mania or depression associated with bipolar disorders and mood disorders associated with schizophrenia, (Pralong E T et al., 2002, Prog. Neurobiol., 67: 173-202), autistic disorders (Carlsson M L, 1998, J. Neural Transm. 105: 525-535), cognitive disorders such as dementias, including age related dementia and senile dementia of the Alzheimer type, memory disorders in a mammal, including a human, attention deficit disorders and pain (Armer R E and Miller D J, 2001, Exp. Opin. Ther. Patents, 11 (4): 563-572).

Thus, increasing activation of NMDA receptors via GlyT-1 inhibition may lead to agents that treat psychosis, schizophrenia, dementia and other diseases in which cognitive processes are impaired, such as attention deficit disorders or Alzheimer's disease.

SUMMARY OF THE INVENTION

The present invention provides compounds of formula I

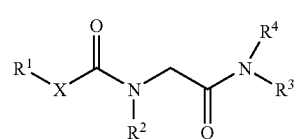

wherein $R^1$ is lower alkyl, aryl or heteroaryl, wherein aryl and heteroaryl are optionally substituted by halogen, lower alkyl, lower alkoxy, lower alkyl substituted by halogen, lower alkoxy substituted by halogen, cyano, amino, di-lower alkyl amino or morpholinyl;

$R^2$ is lower alkyl, —$(CH_2)_n$-aryl, —$(CH_2)_n$-heteroaryl or —$(CH_2)_n$-cycloalkyl, wherein the aryl or heteroaryl groups are optionally substituted by one or more substituents selected from the group consisting of halogen, lower alkyl, cyano, or lower alkoxy;

$R^3$ is hydrogen or lower alkyl;

$R^4$ is aryl or heteroaryl, wherein aryl and heteroaryl are optionally substituted by one or more substituents selected from the group consisting of halogen, lower alkyl substituted by halogen, lower alkoxy substituted by halogen, lower alkyl;

X is a bond or —$OCH_2$—;

n is 0, 1 or 2;

or pharmaceutically acceptable acid addition salts thereof, with the exception of 4-methoxy-N-[2-oxo-2-(phenylamino)ethyl]-N-phenyl-benzamide, 4-chloro-N-[2-[(4-methylphenyl)amino]-2-oxoethyl]-N-phenyl-benzamide, 4-chloro-N-[2-[5-chloro-2-methoxyphenyl)amino]-2-oxoethyl]-N-phenylmethyl-benzamide, 4-methyl-N-(2-oxo-2-[(2,4,6-trichlorophenyl)amino]ethyl]-N-phenylmethyl-benzamide, N-[2-[(4-methylphenyl)amino]-2-oxoethyl]-N-phenyl-benzamide, 4-methyl-N-[2-[(4-methylphenyl)amino]-2-oxoethyl]-N-phenyl-benzamide, 4-chloro-N-(2-oxo-2-[(2,4,6-trichlorophenyl)amino]ethyl]-N-phenylmethyl-benzamide and N-[2-[(2, 4-dimethoxyphenyl)amino]-2-oxoethyl]-N-[(2-fluorophenyl)methyl]-benzeneacetamide.

The first excepted compound has been described in *Journal of the Chemical Society, Perkin Transactions* 1: *Organic and Bio-Organic Chemistry* (1972), (7), 909-13 in a cyclisation process of α-acylamino-acids. The other excepted compounds have been listed in the CAS registry file.

Furthermore, the invention includes all racemic mixtures, all their corresponding enantiomers and/or optical isomers.

The present invention also provides pharmaceutical compositions containing a compound of formula I or a pharmaceutical salt thereof. The invention also provides methods for the preparation of the compounds and compositions of the invention.

Compounds of general formula I are good inhibitors of the glycine transporter 1 (GlyT-1) and have a good selectivity to glycine transporter 2 (GlyT-2) inhibitors. The invention provides methods for the treatment of diseases related to activation of NMDA receptors via GlyT-1 inhibition, such as psychoses, dysfunction in memory and learning, schizophrenia, dementia and other diseases in which cognitive processes are impaired, such as attention deficit disorders or Alzheimer's disease. The preferred indications of the present invention are schizophrenia, cognitive impairment and Alzheimer's disease.

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a saturated straight- or branched-chain hydrocarbon group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

The term "cycloalkyl" denotes a saturated or partially saturated carbocyclic ring containing from 3 to 7 carbon atoms, for example cyclopropyl, cyclopentyl, cyclopentenyl, cyclohexyl, cyclohexenyl, cycloheptyl or cycloheptenyl.

The term "halogen" denotes chlorine, iodine, fluorine and bromine.

The term "aryl" denotes a monovalent cyclic aromatic hydrocarbon radical having 6 to 12 ring atoms and consisting of one or more fused rings in which at least one ring is aromatic in nature, for example phenyl or naphthyl.

The term "heteroaryl" denotes a cyclic aromatic hydrocarbon radical, containing one, two or three heteroatoms selected from the group consisting of oxygen, sulphur or nitrogen wherein at least one ring is aromatic in nature, for example pyridyl, quinoxalinyl, dihydrobenzofuranyl, thiophenyl, benzothiophenyl, isoxazolyl, pyrazinyl, pyrimidinyl, pyridazinyl, triazinyl, thiazolyl, pyrrolyl, imidazolyl, pyrazolyl, oxazolyl and isothiazolyl.

The term "lower alkyl substituted by halogen" denotes a lower alkyl group as defined above, wherein at least one hydrogen atom is replaced by a halogen atom, for example the following groups: $CF_3$, $CHF_2$, $CH_2F$, $CH_2CF_3$, $CH_2CHF_2$, $CH_2CH_2F$, $CH_2CH_2CF_3$, $CH_2CH_2CH_2CF_3$, $CH_2CH_2Cl$, $CH_2CF_2CF_3$, $CH_2CF_2CHF_2$, $CF_2CHFCF_3$, $C(CH_3)_2CF_3$, $CH(CH_3)CF_3$ or $CH(CH_2F)CH_2F$.

The term "lower alkoxy" denotes a alkyl group wherein the lower alkyl residue is as defined above and which is attached via an oxygen atom.

The term "lower alkoxy substituted by halogen" denotes an alkoxy group, wherein at least one hydrogen atom is replaced by halogen as defined above.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

"Therapeutically effective amount" means an amount that is effective to prevent, alleviate or ameliorate symptoms of disease or prolong the survival of the subject being treated.

The present invention provides compounds of formula I

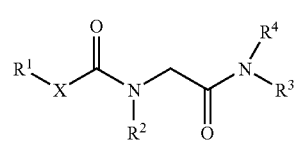

I wherein $R^1$ is lower alkyl, aryl or heteroaryl, wherein aryl and heteroaryl are optionally substituted by halogen, lower alkyl, lower alkoxy, lower alkyl substituted by halogen, lower alkoxy substituted by halogen, cyano, amino, di-lower alkyl amino or morpholinyl;

R² is lower alkyl, —(CH₂)ₙ-aryl, —(CH₂)ₙ-heteroaryl or —(CH₂)ₙ-cycloalkyl, wherein the aryl or heteroaryl groups are optionally substituted by one or more substituents selected from the group consisting of halogen, lower alkyl, cyano, or lower alkoxy;

R³ is hydrogen or lower alkyl;

R⁴ is aryl or heteroaryl, wherein aryl and heteroaryl are optionally substituted by one or more substituents selected from the group consisting of halogen, lower alkyl substituted by halogen, lower alkoxy substituted by halogen, lower alkyl;

X is a bond or —OCH₂—;

n is 0, 1 or 2;

or pharmaceutically acceptable acid addition salts thereof, with the exception of 4-methoxy-N-[2-oxo-2-(phenylamino)ethyl]-N-phenyl-benzamide, 4-chloro-N-[2-[(4-methylphenyl)amino]-2-oxoethyl]-N-phenyl-benzamide, 4-chloro-N-[2-[5-chloro-2-methoxyphenyl)amino]-2-oxoethyl]-N-benzamide, 4-methyl-N-(2-oxo-2-[(2,4,6-trichlorophenyl)amino]ethyl]-N-benzamide, N-[2-[(4-methylphenyl)amino]-2-oxoethyl]-N-phenyl-benzamide, 4-methyl-N-[2-[(4-methylphenyl)amino]-2-oxoethyl]-N-phenyl-benzamide, 4-chloro-N-(2-oxo-2-[(2,4,6-trichlorophenyl)amino]ethyl]-N-benzamide and N-[2-[(2,4-dimethoxyphenyl)amino]-2-oxoethyl]-N-[(2-fluorophenyl)methyl]-benzeneacetamide.

Preferred compounds of formula I are those, wherein X is a bond.

Preferred compounds of formula I of the present invention are further those, wherein R¹ and R⁴ are both monosubstituted aryl, preferably halogen substituted phenyl, for example the following compounds:

4-Chloro-N-[(3-chloro-phenylcarbamoyl)-methyl]-N-(2,6-difluoro-benzyl)-benzamide, 4-Chloro-N-[(3-chloro-phenylcarbamoyl)-methyl]-N-(2,3-difluoro-benzyl)-benzamide, 4-Chloro-N-[(3-chloro-phenylcarbamoyl)-methyl]-N-(2-fluoro-benzyl)-benzamide, 4-Chloro-N-[(3-chloro-phenylcarbamoyl)-methyl]-N-thiophen-2-ylmethyl-benzamide, 4-Chloro-N-[(3-chloro-phenylcarbamoyl)-methyl]-N-(2-methoxy-benzyl)-benzamide, 4-Chloro-N-(3-chloro-benzyl)-N-[(3-chloro-phenylcarbamoyl)-methyl]-benzamide and 4-Chloro-N-(2-chloro-benzyl)-N-[(3-chloro-phenylcarbamoyl)-methyl]-benzamide.

Further preferred compounds are those, wherein R¹ and R⁴ are both monosubstituted aryl, for R¹ preferably methoxy substituted phenyl and for R⁴ preferably halogen substituted phenyl, for example the following compounds:

N-[(3-Chloro-phenylcarbamoyl)-methyl]-N-(2,6-difluorobenzyl)-4-methoxy-benzamide and N-(3-Chloro-benzyl)-N-[(3-chloro-phenylcarbamoyl)-methyl]-4-methoxy-benzamide.

Preferred compounds of formula I of the present invention are further those, wherein R¹ is heteroaryl, preferably benzothiophenyl, for example the following compounds:

Benzo[b]thiophene-2-carboxylic acid (2-chloro-benzyl)-[(3-trifluoromethyl-phenylcarbamoyl)-methyl]-amide, Benzo[b]thiophene-2-carboxylic acid (2-chloro-benzyl)-[(3-fluoro-phenylcarbamoyl)-methyl]-amide, Benzo[b]thiophene-2-carboxylic acid (3,5-difluoro-benzyl)-[(3-fluoro-phenylcarbamoyl)-methyl]-amide, Benzo[b]thiophene-2-carboxylic acid [(3-chloro-4-fluoro-phenylcarbamoyl)-methyl]-(2,6-difluoro-benzyl)-amide, Benzo[b]thiophene-2-carboxylic acid [(3-chloro-4-fluoro-phenylcarbamoyl)-methyl]-(2,3-difluoro-benzyl)-amide and Benzo[b]thiophene-2-carboxylic acid [(3-chloro-4-fluoro-phenylcarbamoyl)-methyl]-(3,5-difluoro-benzyl)-amide.

Preferred compounds of formula I of the present invention are further those, wherein R¹ and R⁴ are monosubstituted aryl, preferably halogen substituted phenyl for R¹ and CF₃ substituted phenyl for R⁴, for example the following compound:

N-(2-Chloro-benzyl)-4-fluoro-N-[(3-trifluoromethyl-phenylcarbamoyl)-methyl]-benzamide.

The present compounds of formula I and their pharmaceutically acceptable salts can be prepared by methods known in the art, for example, by processes described below, which processes comprise a) reacting a compound of formula

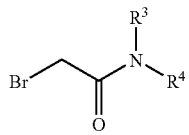

III with a compound of formula

II and with a compound of formula

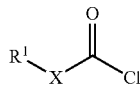

IV in the presence of N-ethyldiisopropylamine to produce a compound of formula

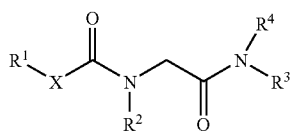

I wherein the substituents are as defined above, or b) reacting a compound of formula

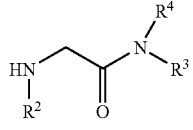

V with a compound of formula

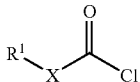

in presence of triethylamine to produce a compound of formula

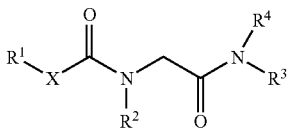

wherein the substituents are as defined above or c) reacting a compound of formula

      IX with a compound of formula

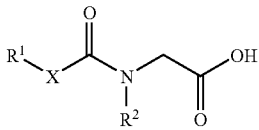      VIII in the presence of N-ethyldiisopropylamine and HATU [O-(7-Azabenzotriazole-1-yl)-N, N,N'N'-tetramethyluronium hexafluorophosphate], to produce a compound of formula

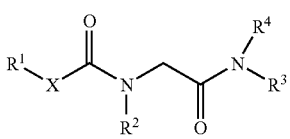      I wherein the substituents are as defined above, or d) reacting a compound of formula

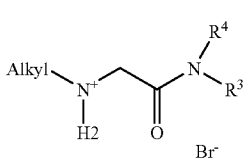      V-1 with a compound of formula

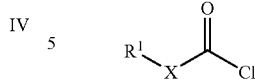      IV in the presence of triethylamine, to produce a compound of formula

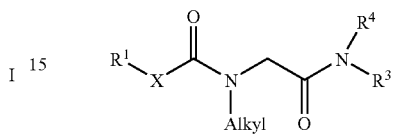      I wherein the substituents are as defined above and if desired, converting the compounds obtained into pharmaceutically acceptable acid addition salts.

The acid addition salts of the basic compounds of formula I can be converted to the corresponding free bases by treatment with at least a stoichiometric equivalent of a suitable base such as sodium or potassium hydroxide, potassium carbonate, sodium bicarbonate, ammonia, and the like.

The compounds of formula I can be prepared in accordance with process variant a) to d), with the following schemes and with working examples 1-128.

The starting material is commercially available or can be prepared in accordance with known methods.

Procedure A

This procedure is used to prepare Example 34 (N-phenyl-N-(p-tolylcarbamoyl-methyl)-6-trifluoromethyl-nicotinamide).

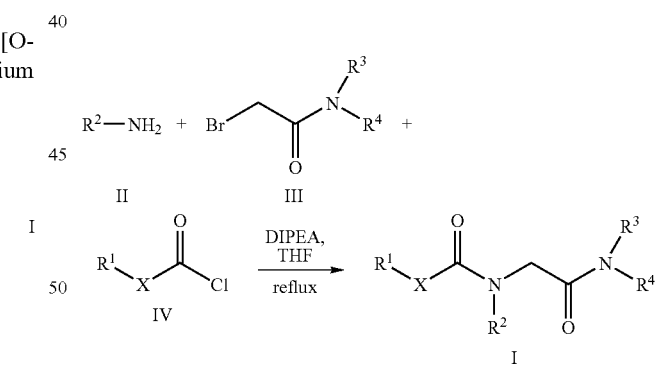

To a compound of formula III, for example 2-bromo-N-(4-methyl-phenyl)-acetamide, in THF is added a compound of formula II, for example aniline and N-ethyldiisopropylamine, and a compound of formula IV, for example 6-trifluoromethyl-nicotynoyl chloride, and the reaction mixture is stirred over night at reflux. Then the reaction is concentrated in vacuo, and the reaction mixture is purified in conventional manner.

Procedure B

This procedure is used to prepare Example 30: N-[(3,4-dichloro-phenylcarbamoyl)-methyl]-N-phenyl-3-trifluoromethyl benzamide.

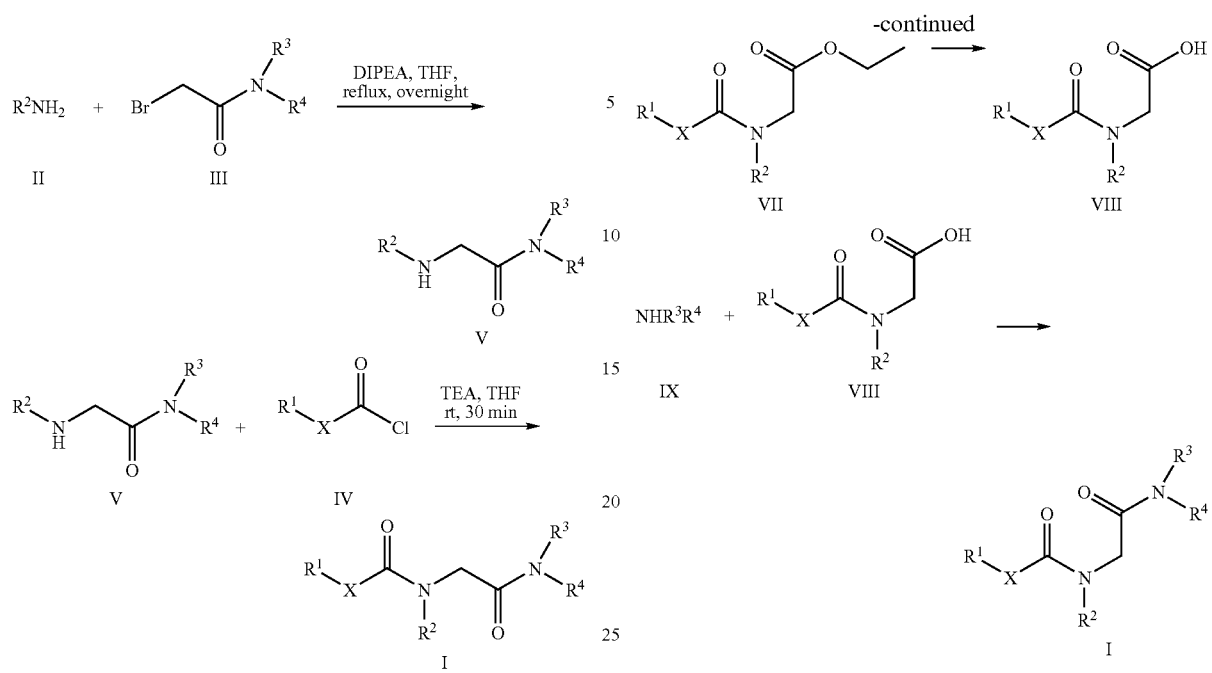

Step 1: Compound of Formula V

To a compound of formula III, for example 2-bromo-N-(3,4-dichloro-phenyl)-acetamide, in THF is added a compound of formula II, for example aniline and N-ethyldiisopropylamine, and the reaction mixture is stirred over night at reflux. The precipitated salt is then filtered off, and the filtrate was then concentrated in vacuo. The residue was then purified in conventional manner.

Step 2: Compound of Formula I

To a compound of formula V, for example N-(3,4-dichloro-phenyl)-2-phenylamino-acetamide, in THF is added triethylamine and a compound of formula IV, for example 3-trifluoromethylbenzoyl chloride, and the reaction mixture is stirred at room temperature for about 30 minutes. Water is then added to the mixture until precipitation occurred, and the mixture is stirred for 5 minutes. Then the precipitate is isolated by filtration and washed.

Procedure C

This procedure is used to prepare Example 30: 4-chloro-N-[(3-chloro-phenylcarbamoyl)-methyl]-N-(2-fluoro-benzyl)benzamide.

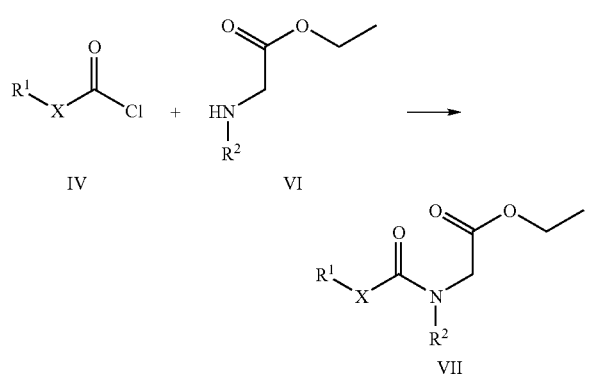

Step 1: Compound of Formula VII

To a compound of formula VI, for example (2,6-dichloro-benzylamino)-acetic acid ethyl ester, in suspension THF is added triethylamine and a compound of formula IV, for example 4-methoxybenzoyl chloride, and the reaction mixture is stirred at room temperature for 10 min. Water is then added to the reaction mixture, and the aqueous phase is extracted with diethylacetate. The combined organic phases are then dried, concentrated in vacuo and purified.

Step 2: Compound of Formula VIII

To a compound of formula VII, for example N-(3,4-dichloro-phenyl)-2-phenylamino-acetamide, in ethanol is added NaOH, and the reaction mixture is stirred at room temperature for about 3 hours. The reaction mixture is then neutralized by addition of HCl, and the ethanol is eliminated by evaporation. Water and ethyl acetate is then added to the residue. The organic phase is separated, and the aqueous phase is extracted with ethylacetate. The combined organic phase is then washed again with water, dried and concentrated in vacuo.

Step 3: Compound of Formula I

To a solution of a compound of formula IX, for example 3-chloroaniline, in DMF is added N-ethyldiiopropylamine, a compound of formula VIII, for example [(2,6-dichloro-benzyl)-(4-methoxy-benzoyl)-amino]-acetic acid, and HATU; and the reaction mixture is stirred at room temperature over night. Then water is added until precipitation occurs, and the precipitate is isolated by filtration and washed with a mixture of water and ethanol to yield the title compound.

Procedure D

This procedure was used to prepare Example 1: 4-chloro-N-[(3-chloro-phenylcarbamoyl)-methyl]-N-(2,6-difluoro-benzyl)-benzamide.

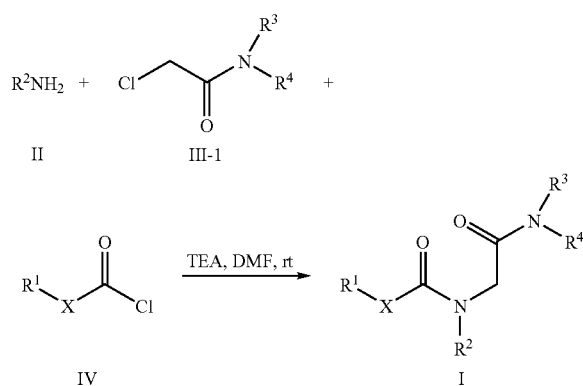

To a compound of formula III-1, for example N-1-(3-chlorophenyl)-2-chloroacetamide, in DMF is added a compound of formula II, for example 2,6-difluorobenzylamine and triethylamine, and a compound of formula IV, such as 4-chlorobenzoyl chloride. The reaction mixture is stirred at room temperature for about 15 min and then purified.

Procedure E

This procedure was used to prepare Example 97: N-[(3,4-dichloro-phenylcarbamoyl)-methyl]-N-isobutyl-4-methoxy-benzamide.

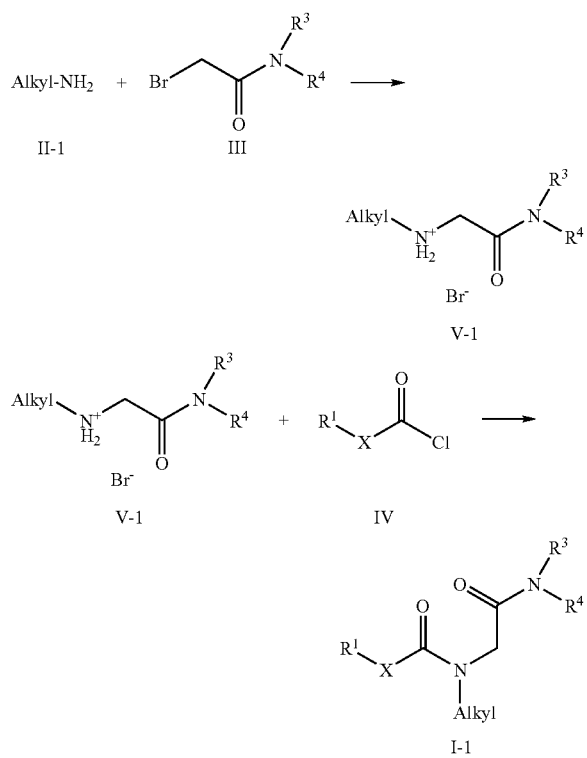

Step 1: Hydrobromide of a Compound of Formula V-1

To a solution of a compound of formula III, for example 2-bromo-N-(3,4-dichloro-phenyl)-acetamide, in dichloromethane at 0° C. is slowly added isobutylamine in dichloromethane. The reaction mixture is allowed to warm up to room temperature and then stirred for another 24 hours. Then the salt is filtered off and the filtrate is concentrated in vacuo. The residue is then purified.

Step 2: Compound of Formula I-1.

To a solution of a compound of formula V-1, such as N-(3,4-dichloro-phenyl)-2-isobutylamino-acetamide hydrobromide, in THF are slowly added a solution of triethylamine in THF and a solution of a compound of formula IV, for example 4-methoxybenzoyl chloride, in THF, and the reaction mixture is stirred at room temperature for about 24 hours. Then water is added to the reaction mixture, and the precipitate is isolated by filtration and then purified.

The compounds of formula I and their pharmaceutically usable addition salts possess valuable pharmacological properties. Specifically, the compounds of the present invention are good inhibitors of the glycine transporter I (GlyT-1).

The compounds were investigated in accordance with the test given hereinafter.

Solutions and Materials

DMEM complete medium: Nutrient mixture F-12 (Gibco Life-technologies), fetal bovine serum (FBS) 5%, (Gibco life technologies), Penicillin/Streptomycin 1% (Gibco life technologies), Hygromycin 0.6 mg/ml (Gibco life technologies), Glutamine 1 mM Gibco life technologies)

Uptake buffer (UB): 150 mM NaCl, 10 mM Hepes-Tris, pH 7.4, 1 mM $CaCl_2$, 2.5 mM KCl, 2.5 mM $MgSO_4$, 10 mM (+) D-glucose.

Flp-in™-CHO (Invitrogen Cat n° R758-07) cells stably transfected with mGlyT1b cDNA.

Glycine Uptake Inhibition Assay (mGlyT-1b)

On day 1 mammalian cells, (Flp-in™-CHO), transfected with mGlyT-1b cDNA, were plated at the density of 40,000 cells/well in complete F-12 medium, without hygromycin in 96-well culture plates. On day 2, the medium was aspirated and the cells were washed twice with uptake buffer (UB). The cells were then incubated for 20 min at 22° C. with either (i) no potential competitor, (ii) 10 mM non-radioactive glycine, (iii) a concentration of a potential inhibitor. A range of concentrations of the potential inhibitor was used to generate data for calculating the concentration of inhibitor resulting in 50% of the effect (e.g. $IC_{50}$, the concentration of the competitor inhibiting glycine uptake of 50%). A solution was then immediately added containing [$^3$H]-glycine 60 nM (11-16 Ci/mmol) and 25 μM non-radioactive glycine. The plates were incubated with gentle shaking and the reaction was stopped by aspiration of the mixture and washing (three times) with ice-cold UB. The cells were lysed with scintillation liquid, shaken 3 hours and the radioactivity in the cells was counted using a scintillation counter.

The compounds described in examples 1-128 have an $IC_{50}$ data <1.0 μM. The $IC_{50}$ data (<0.4 μM) for representative compounds 1-128 is be provided in table 2.

The present invention also provides pharmaceutical compositions containing compounds of the invention, for example compounds of formula I and their pharmaceutically suitable acid addition salts, and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compounds of the invention, in addition to one or more compounds of the invention, contain a pharmaceutically acceptable carrier. Suitable pharmaceutically acceptable carriers include pharmaceutically inert, inorganic and organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are however usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The invention also provides a method for preparing compositions of the invention which comprises bringing one or more compounds of formula I and/or pharmaceutically acceptable acid addition salts and, if desired, one or more other therapeutically valuable substances into a galenical administration form together with one or more therapeutically inert carriers.

The most preferred indications in accordance with the present invention are those, which include disorders of the central nervous system, for example the treatment or prevention of schizophrenia, cognitive impairment and Alzheimer's disease. The invention provides a method for the treatment of schizophrenia, which comprises administering to an individual a therapeutically effective amount of a compound of formula I or a pharmaceutically acceptable salt thereof. The invention also provides a method for the treatment of Alzheimer's disease, which comprises administering to an individual a therapeutically effective amount of a compound of formula I or a pharmaceutically acceptable salt thereof. The invention further comprises a method for improving cognition, which comprises administering to an individual a therapeutically effective amount of a compound of formula I or a pharmaceutically acceptable salt thereof.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

Tablet Formulation (Wet Granulation)

| | | mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| | | mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

The following examples illustrate the present invention without limiting it. All temperatures are given in degree Celsius.

Procedure A

This procedure is used to prepare Example 34

N-Phenyl-N-(p-tolylcarbamoyl-methyl)-6-trifluoromethyl-nicotinamide

To 2-bromo-N-(4-methyl-phenyl)-acetamide (100 mg) in THF (3.0 mL) was added aniline (41 mg) and N-ethyldiisopropylamine and 6-trifluoromethyl-nicotynoyl chloride (110 mg) the reaction mixture was stirred over night at reflux. Then the reaction was concentrated in vacuo and the reaction mixture was purified by column chromatography to yield the title compound as a light brown solid (127 mg, 70%).

Procedure B

This procedure was used to prepare Example 30

N-[(3,4-Dichloro-phenylcarbamoyl)-methyl]-N-phenyl-3-trifluoromethyl benzamide

Step 1:
N-(3,4-Dichloro-phenyl)-2-phenylamino-acetamide

To 2-bromo-N-(3,4-dichloro-phenyl)-acetamide (2 g) in THF (80 mL) was added aniline (41 mg) and N-ethyldiisopropylamine and the reaction mixture was stirred over night at reflux. The precipitated salt was then filtered off and the filtrate was then concentrated in vacuo. The residue was then purified by column chromatography to give the title compound as a light brown solid (1.3 g, mp=110-112° C.).

Step 2: N-[(3,4-Dichloro-phenylcarbamoyl)-methyl]-N-phenyl-3-trifluoromethyl benzamide To N-(3,4-dichloro-phenyl)-2-phenylamino-acetamide (73 mg) in THF (3.1 mL) was added tiethylamine (52 μL) and 3-trifluoromethylbenzoyl chloride (62 mg) and the reaction mixture was stirred at room temperature for 30 minutes. To the mixture was then added water under precipitation occurred and the mixture was stirred for 5 minutes. Then the precipitate was isolated by filtration and washed with a mixture water-ethanol (1:1) to yield the title compound as a white solid (64 mg, mp=130-132° C.).

Procedure C

This procedure was used to prepare Example 30

4-Chloro-N-[(3-chloro-phenylcarbamoyl)-methyl]-N-(2-fluoro-benzyl)benzamide

Step 1: N-(3,4-Dichloro-phenyl)-2-phenylamino-acetamide

To (2,6-dichloro-benzylamino)-acetic acid ethyl ester (100 mg) in suspension THF (5 mL) was added triethylamine (0.08 mL) and 4-methoxybenzoyl chloride (78 mg) and the reaction mixture was stirred at room temperature for 10 min. After such time the water was added to the reaction mixture and the aqueous phase was extracted with diethylacetate. The combined organic phases were then dried over sodium sulfate, concentrated vacuo and purified by column chromatography to yield the title (128 mg). MS (m/e): 396.3 (M+H$^+$)

Step 2: [(2,6-Dichloro-benzyl)-(4-methoxy-benzoyl)-amino]-acetic acid

To N-(3,4-dichloro-phenyl)-2-phenylamino-acetamide in ethanol (10 mL) was added 1N NaOH (0.38 μL) and the reaction mixture was stirred at room temperature for 3 hours. After such time the reaction mixture was neutralized by addition of 3N HCl and the ethanol was eliminated by evaporation. To the residue was added more water and ethyl acetate. The organic phase was separated and the aqueous phase was extracted with ethylacetate. The combined organic phase was then washed again with water, dried over sodium sulfate and concentrated in vacuo to yield the title compound (90 mg). MS (m/e): 366.0 (M−H).

Step 3: 4-Chloro-N-[(3-chloro-phenylcarbamoyl)-methyl]-N-(2-fluoro-benzyl)benzamide To a solution of 3-chloroaniline (20 mg) in DMF (1.5 mL) was added N-ethyldiiopropylamine (137 μL), [(2,6-Dichloro-benzyl)-(4-methoxy-benzoyl)-amino]-acetic acid (58 mg) and HATU (Across 365312) and the reaction mixture was stirred at room temperature over night. Then water was added until the precipitation occurs and the precipitation was isolated by filtration and washed with a mixture of water and ethanol (2:1) to yield the title compound (35 mg). MS (m/e): 479.2 (M+H$^+$).

Procedure D

This procedure was used to prepare Example 1

4-Chloro-N-[(3-chloro-phenylcarbamoyl)-methyl]-N-(2,6-difluoro-benzyl)-benzamide To N1-(3-chlorophenyl)-2-chloroacetamide (61 mg) in DMF (1 mL) was added 2,6-difluorobenzylamine (38 mg) and triethylamine (0.1 mL) and 4-chlorobenzoyl chloride (58 mg) the reaction mixture was stirred at room temperature for 15 min and then purified by HPLC preparative to yield the title compound (55 mg). MS (m/e): 447.0 (M−H).

Procedure E

This procedure was used to prepare Example 97

N-[(3,4-Dichloro-phenylcarbamoyl)-methyl]-N-isobutyl-4-methoxy-benzamide

Step 1: N-(3,4-Dichloro-phenyl)-2-isobutylamino-acetamide hydrobromide

To a solution of 2-bromo-N-(3,4-dichloro-phenyl)-acetamide (0.1 g) in dichloromethane (80 mL) at 0° C. was slowly added of isobutylamine (52 mg) in dichloromethane. The reaction mixture was allowed to warm up to room temperature and then stirred for another 24 hours. Then the salt was filtered off and the filtrate was concentrated in vacuo. The residue was then purified by column chromatography to yield the title compound as a white solid (0.1 g). MS (m/e): 357.1 (M+H$^+$).

Step 2: N-[(3,4-Dichloro-phenylcarbamoyl)-methyl]-N-isobutyl-4-methoxy-benzamide To a solution of N-(3,4-dichloro-phenyl)-2-isobutylamino-acetamide hydrobromide (0.090 g) in THF were slowly added a solution of triethylamine (0.064 mg) in THF (5 mL) and a solution of 4-methoxybenzoyl chloride (47 mg) in THF (5 mL) and the reaction mixture was stirred at room temperature for 24 hours. Then water was added to the reaction mixture and the precipitate was isolated by filtration and then purified by column chromatography to yield the title compound (78 mg). MS (m/e): 409.2 (M−H, 100%).

The following starting materials for preparation of compounds of formula I have been used:

TABLE 1

| Exp | Procedure | Amine/Aniline | Chloro amide or bromo amide | Acyl chloride |
|---|---|---|---|---|
| 1 | D | 2,6-Difluorobenzylamine | N1-(3-Chlorophenyl)-2-chloroacetamide | 4-Chlorobenzoyl chloride |
| 2 | D | 3,4-Difluorobenzylamine | N1-(3-Chlorophenyl)-2-chloroacetamide | 4-Chlorobenzoyl chloride |
| 3 | D | 3,5-Difluorobenzylamine | N1-(3-Chlorophenyl)-2-chloroacetamide | 4-Chlorobenzoyl chloride |
| 4 | D | 2,3-Difluorobenzylamine | N1-(3-Chlorophenyl)-2-chloroacetamide | 4-Chlorobenzoyl chloride |

TABLE 1-continued

| Exp | Procedure | Amine/Aniline | Chloro amide or bromo amide | Acyl chloride |
|---|---|---|---|---|
| 5 | D | 2,4-Difluorobenzylamine | N1-(3-Chlorophenyl)-2-chloroacetamide | 4-Chlorobenzoyl chloride |
| 6 | D | 2,5-Difluorobenzylamine | N1-(3-Chlorophenyl)-2-chloroacetamide | 4-Chlorobenzoyl chloride |
| 7 | D | 4-Fluorobenzylamine | N1-(3-Chlorophenyl)-2-chloroacetamide | 4-Chlorobenzoyl chloride |
| 8 | D | 3-Fluorobenzylamine | N1-(3-Chlorophenyl)-2-chloroacetamide | 4-Chlorobenzoyl chloride |
| 9 | D | 2-Fluorobenzylamine | N1-(3-Chlorophenyl)-2-chloroacetamide | 4-Chlorobenzoyl chloride |
| 10 | D | Thiophen-3-yl-methylamine | N1-(3-Chlorophenyl)-2-chloroacetamide | 4-Methoxybenzoyl chloride |
| 11 | D | 2,6-Difluorobenzylamine | N1-(3-Chlorophenyl)-2-chloroacetamide | 4-Methoxybenzoyl chloride |
| 12 | D | 3,5-Dichlorobenzylamine | N1-(3-Chlorophenyl)-2-chloroacetamide | 4-Methoxybenzoyl chloride |
| 13 | D | 2,6-Dichlorobenzylamine | N1-(3-Chlorophenyl)-2-chloroacetamide | 4-Methoxybenzoyl chloride |
| 14 | D | 3-Chlorobenzylamine | N1-(3-Chlorophenyl)-2-chloroacetamide | 4-Methoxybenzoyl chloride |
| 15 | D | Benzylamine | N1-(3-Chlorophenyl)-2-chloroacetamide | 4-Fluorobenzoyl chloride |
| 16 | D | benzylamine | N1-(3-Chlorophenyl)-2-chloroacetamide | 4-Chlorobenzoyl chloride |
| 17 | D | Thiophen-2-yl-methylamine | N1-(3-Chlorophenyl)-2-chloroacetamide | 4-Chlorobenzoyl chloride |
| 18 | D | Thiophen-2-yl-methylamine | N1-(3-Chlorophenyl)-2-chloroacetamide | 4-Methoxybenzoyl chloride |
| 19 | C | (2,6-Dichloro-benzylamino)-acetic acid ethyl ester | 3-Chloro aniline | 4-Methoxybenzoyl chloride |
| 20 | D | 3-Fluoroaniline | 2-Bromo-N-(3,4-dichloro-phenyl)-acetamide | 4-Methoxybenzoyl chloride |
| 21 | D | 2-Fluoroaniline | 2-Bromo-N-(3,4-dichloro-phenyl)-acetamide | 4-Methoxybenzoyl chloride |
| 22 | B | Aniline | 2-Bromo-N-(3,4-dichloro-phenyl)-acetamide | 4-Methoxybenzoyl chloride |
| 23 | C | Phenylamino-acetic acid ethyl ester | 3-Chloro-2-Fluoroaniline | 4-Methoxybenzoyl chloride |
| 24 | C | Phenylamino-acetic acid ethyl ester | 5-Amino-2,2-difluoro-1,3-benzodioxole | 4-Methoxybenzoyl chloride |
| 25 | C | Phenylamino-acetic acid ethyl ester | 3-(Trifluoromethoxy)aniline | 4-Methoxybenzoyl chloride |
| 26 | C | Phenylamino-acetic acid ethyl ester | m-Toluidine | 4-Methoxybenzoyl chloride |
| 27 | C | Phenylamino-acetic acid ethyl ester | 3-Aminobenzotrifluoride | 4-Methoxybenzoyl chloride |
| 28 | C | Phenylamino-acetic acid ethyl ester | 3-Chloroaniline | 4-Methoxybenzoyl chloride |
| 29 | C | Phenylamino-acetic acid ethyl ester | 3-methoxybenzonitrile | 4-Methoxybenzoyl chloride |
| 30 | B | Aniline | 2-Bromo-N-(3,4-dichloro-phenyl)-acetamide | 3-trifluoromethylbenzoyl chloride |
| 31 | B | Aniline | 2-Bromo-N-(3,4-dichloro-phenyl)-acetamide | 3-cyanobenzoyl chloride |
| 32 | B | Aniline | 2-Bromo-N-(3,4-dichloro-phenyl)-acetamide | 2-Methoxybenzoyl chloride |
| 33 | B | Aniline | 2-Bromo-N-(3,4-dichloro-phenyl)-acetamide | 3-Methylbenzoyl chloride |
| 34 | A | Aniline | 2-Bromo-N-(4-methyl-phenyl)-acetamide | 6-trifluoromethyl-nicotynoyl chloride |
| 35 | B | Aniline | 2-Bromo-N-(3,4-dichloro-phenyl)-acetamide | 3-Chlorobenzoyl chloride |
| 36 | A | Aniline | 2-Bromo-N-(4-fluoro-phenyl)-acetamide | 6-trifluoromethyl-nicotynoyl chloride |
| 37 | B | Aniline | 2-Bromo-N-(3,4-dichloro-phenyl)-acetamide | 6-Trifluoromethyl-nicotinoyl chloride |

TABLE 1-continued

| Exp | Procedure | Amine/Aniline | Chloro amide or bromo amide | Acyl chloride |
|---|---|---|---|---|
| 38 | B | Aniline | 2-Bromo-N-(3,4-dichloro-phenyl)-acetamide | 4-cyanobenzoyl chloride |
| 39 | B | Aniline | 2-Bromo-N-(3,4-dichloro-phenyl)-acetamide | 2-Fluorobenzoyl chloride |
| 40 | B | Aniline | 2-Bromo-N-(3,4-dichloro-phenyl)-acetamide | 3-fluorobenzoyl chloride |
| 41 | B | Aniline | 2-Bromo-N-(3,4-dichloro-phenyl)-acetamide | 4-methoxybenzoyl chloride |
| 42 | B | Aniline | 2-Bromo-N-(3,4-dichloro-phenyl)-acetamide | 4-fluorobenzoyl chloride |
| 43 | D | 2-Chloro-benzylamine | 2-Chloro-N-(3-trifluoromethyl-phenyl)-acetamide | 3-Methylbenzoyl chloride |
| 44 | D | 2-Chloro-benzylamine | 2-Chloro-N-(3-trifluoromethyl-phenyl)-acetamide | 6-trifluoromethyl-nicotynoyl chloride |
| 45 | D | 3,5-difluoro-benzylamine | 2-Chloro-N-(3-trifluoromethyl-phenyl)-acetamide | 3-Chlorobenzoyl chloride |
| 46 | D | 3,5-difluoro-benzylamine | 2-Chloro-N-(3-trifluoromethyl-phenyl)-acetamide | 6-trifluoromethyl-nicotynoyl chloride |
| 47 | D | 3,5-difluoro-benzylamine | 2-Chloro-N-(3-trifluoromethyl-phenyl)-acetamide | 6-Trifluoromethyl-nicotinoyl chloride |
| 48 | D | 3,5-difluoro-benzylamine | 2-Chloro-N-(3-trifluoromethyl-phenyl)-acetamide | 4-cyanobenzoyl chloride |
| 49 | D | 3,5-difluoro-benzylamine | 2-Chloro-N-(3-trifluoromethyl-phenyl)-acetamide | 2-Fluorobenzoyl chloride |
| 50 | D | 3,5-difluoro-benzylamine | 2-Chloro-N-(3-trifluoromethyl-phenyl)-acetamide | 4-cyanobenzoyl chloride |
| 51 | D | 2-Chloro-benzylamine | 2-Chloro-N-(3-trifluoromethyl-phenyl)-acetamide | Benzo[b]thiophene-2-carbonyl chloride |
| 52 | D | 2-Chloro-benzylamine | 2-Chloro-N-(3-trifluoromethyl-phenyl)-acetamide | 3-fluorobenzoyl chloride |
| 53 | D | 2-Chloro-benzylamine | 2-Chloro-N-(3-trifluoromethyl-phenyl)-acetamide | 4-Chlorobenzoyl chloride |
| 54 | D | 2-Chloro-benzylamine | 2-Chloro-N-(3-trifluoromethyl-phenyl)-acetamide | 4-trifluoromethoxybenzoyl chloride |
| 55 | D | 2-Chloro-benzylamine | 2-Chloro-N-(3-trifluoromethyl-phenyl)-acetamide | 4-Fluorobenzoyl chloride |
| 56 | D | 3,5-difluoro-benzylamine | 2-Chloro-N-(3-trifluoromethyl-phenyl)-acetamide | 6-trifluoromethyl benzyl chloride |
| 57 | D | 2-Chloro-benzylamine | 2-Chloro-N-(3-fluoro-phenyl)-acetamide | Benzo[b]thiophene-2-carbonyl chloride |
| 58 | D | 2-Chloro-benzylamine | 2-Chloro-N-(3-fluoro-phenyl)-acetamide | 3-fluorobenzoyl chloride |
| 59 | D | 2-Chloro-benzylamine | 2-Chloro-N-(3-fluoro-phenyl)-acetamide | 3-Methylbenzoyl chloride |
| 60 | D | 2-Chloro-benzylamine | 2-Chloro-N-(3-fluoro-phenyl)-acetamide | 4-trifluoromethoxybenzoyl chloride |
| 61 | D | 2-Chloro-benzylamine | 2-Chloro-N-(3-fluoro-phenyl)-acetamide | 4-Fluorobenzoyl chloride |
| 62 | D | 2-Chloro-benzylamine | 2-Chloro-N-(3-fluoro-phenyl)-acetamide | 4-cyanobenzoyl chloride |
| 63 | D | 3,5-difluoro-benzylamine | 2-Chloro-N-(3-fluoro-phenyl)-acetamide | Benzo[b]thiophene-2-carbonyl chloride |
| 64 | D | 3,5-difluoro-benzylamine | 2-Chloro-N-(3-fluoro-phenyl)-acetamide | 3-Methylbenzoyl chloride |

TABLE 1-continued

| Exp | Procedure | Amine/Aniline | Chloro amide or bromo amide | Acyl chloride |
|---|---|---|---|---|
| 65 | D | 3,5-difluoro-benzylamine | 2-Chloro-N-(3-fluoro-phenyl)-acetamide | 4-trifluoromethoxybenzoyl chloride |
| 66 | D | 3,4-difluoro-benzylamine | 2-Chloro-N-(3-fluoro-phenyl)-acetamide | Benzo[b]thiophene-2-carbonyl chloride |
| 67 | D | 3,4-difluoro-benzylamine | 2-Chloro-N-(3-fluoro-phenyl)-acetamide | 3-Methylbenzoyl chloride |
| 68 | D | 3,4-difluoro-benzylamine | 2-Chloro-N-(3-fluoro-phenyl)-acetamide | 4-trifluoromethoxybenzoyl chloride |
| 69 | D | 2,6-difluoro-benzylamine | 2-Chloro-N-(3-Chloro,4-fluoro-phenyl)-acetamide | Benzo[b]thiophene-2-carbonyl chloride |
| 70 | D | 2,6-difluoro-benzylamine | 2-Chloro-N-(3-Chloro,4-fluoro-phenyl)-acetamide | 3-Methylbenzoyl chloride |
| 71 | D | 2,6-difluoro-benzylamine | 2-Chloro-N-(3-Chloro,4-fluoro-phenyl)-acetamide | 4-trifluoromethoxybenzoyl chloride |
| 72 | D | 2-Chloro-benzylamine | 2-Chloro-N-(3-Chloro,4-fluoro-phenyl)-acetamide | Benzo[b]thiophene-2-carbonyl chloride |
| 73 | D | 2-Chloro-benzylamine | 2-Chloro-N-(3-Chloro,4-fluoro-phenyl)-acetamide | 3-fluorobenzoyl chloride |
| 74 | D | 2-Chloro-benzylamine | 2-Chloro-N-(3-Chloro,4-fluoro-phenyl)-acetamide | 4-Chlrorobenzoyl chloride |
| 75 | D | 2-Chloro-benzylamine | 2-Chloro-N-(3-Chloro,4-fluoro-phenyl)-acetamide | 4-trifluoromethoxybenzoyl chloride |
| 76 | D | 2-Chloro-benzylamine | 2-Chloro-N-(3-Chloro,4-fluoro-phenyl)-acetamide | 4-Fluorobenzoyl chloride |
| 77 | D | 2-Chloro-benzylamine | 2-Chloro-N-(3-Chloro,4-fluoro-phenyl)-acetamide | 4-cyanobenzoyl chloride |
| 78 | D | 2,6-difluoro-benzylamine | 2-Chloro-N-(3-Chloro,4-fluoro-phenyl)-acetamide | 4-Fluorobenzoyl chloride |
| 79 | D | 2-Chloro-benzylamine | 2-Chloro-N-(3-Chloro,4-fluoro-phenyl)-acetamide | 6-trifluoromethyl benzyl chloride |
| 80 | D | 2,3-Difluoro-benzylamine | 2-Chloro-N-(3-Chloro,4-fluoro-phenyl)-acetamide | Benzo[b]thiophene-2-carbonyl chloride |
| 81 | D | 2,3-Difluoro-benzylamine | 2-Chloro-N-(3-Chloro,4-fluoro-phenyl)-acetamide | 3-fluorobenzoyl chloride |
| 82 | D | 2,3-Difluoro-benzylamine | 2-Chloro-N-(3-Chloro,4-fluoro-phenyl)-acetamide | 4-Chlrorobenzoyl chloride |
| 83 | D | 2,3-Difluoro-benzylamine | 2-Chloro-N-(3-Chloro,4-fluoro-phenyl)-acetamide | 4-trifluoromethoxybenzoyl chloride |
| 84 | D | 2,3-Difluoro-benzylamine | 2-Chloro-N-(3-Chloro,4-fluoro-phenyl)-acetamide | 4-Fluorobenzoyl chloride |
| 85 | D | 2,3-Difluoro-benzylamine | 2-Chloro-N-(3-Chloro,4-fluoro-phenyl)-acetamide | 4-cyanobenzoyl chloride |
| 86 | D | 2,3-Difluoro-benzylamine | 2-Chloro-N-(3-Chloro,4-fluoro-phenyl)-acetamide | 6-trifluoromethyl benzyl chloride |
| 87 | D | 2,3-Difluoro-benzylamine | 2-Chloro-N-(3-Chloro,4-fluoro-phenyl)-acetamide | Benzo[b]thiophene-2-carbonyl chloride |
| 88 | D | 2,6-difluoro-benzylamine | 2-Chloro-N-(3-Chloro,4-fluoro-phenyl)-acetamide | 4-cyanobenzoyl chloride |
| 89 | D | 2,3-Difluoro-benzylamine | 2-Chloro-N-(3-Chloro,4-fluoro-phenyl)-acetamide | 3-Methylbenzoyl chloride |
| 90 | D | 3,5-difluoro-benzylamine | 2-Chloro-N-(3-Chloro,4-fluoro-phenyl)-acetamide | 4-trifluoromethoxybenzoyl chloride |

TABLE 1-continued

| Exp | Procedure | Amine/Aniline | Chloro amide or bromo amide | Acyl chloride |
|---|---|---|---|---|
| 91 | D | 3,5-difluoro-benzylamine | 2-Chloro-N-(3-Chloro,4-fluoro-phenyl)-acetamide | 4-Fluorobenzoyl chloride |
| 92 | D | 3,5-difluoro-benzylamine | 2-Chloro-N-(3-Chloro,4-fluoro-phenyl)-acetamide | 4-cyanobenzoyl chloride |
| 93 | D | 3,5-difluoro-benzylamine | 2-Chloro-N-(3-Chloro,4-fluoro-phenyl)-acetamide | 6-trifluoromethyl benzyl chloride |
| 94 | D | 3,4-Difluoro-benzylamine | 2-Chloro-N-(3-Chloro,4-fluoro-phenyl)-acetamide | Benzo[b]thiophene-2-carbonyl chloride |
| 95 | D | 2,2-simethyl propylamine | 2-Chloro-N-(3-Chloro phenyl)-acetamide | 4-Chlrorobenzoyl chloride |
| 96 | D | 3,3-dimethyl butylamine | 2-Chloro-N-(3-Chloro phenyl)-acetamide | 4-Chlrorobenzoyl chloride |
| 97 | E | iso butylamine | 2-Bromo-N-(3,4-dichloro phenyl)-acetamide | 4-Methoxybenzoyl chloride |
| 98 | E | 3-methyl butylamine | 2-Bromo-N-(3,4-dichloro phenyl)-acetamide | 4-Methoxybenzoyl chloride |
| 99 | B | benzylamine | 2-Bromo-N-(3,4-dichloro phenyl)-acetamide | 4-Methoxybenzoyl chloride |
| 100 | D | 3-cyano-benzylamine | 2-Chloro-N-(3-chloro-phenyl)-acetamide | 4-Chlorobenzoyl chloride |
| 101 | D | 3-methoxy-benzylamine | 2-Chloro-N-(3-chloro-phenyl)-acetamide | 4-Chlorobenzoyl chloride |
| 102 | D | 2-methoxy-benzylamine | 2-Chloro-N-(3-chloro-phenyl)-acetamide | 4-Chlorobenzoyl chloride |
| 103 | D | 3-methyl-benzylamine | 2-Chloro-N-(3-chloro-phenyl)-acetamide | 4-Chlorobenzoyl chloride |
| 104 | D | 2-methyl-benzylamine | 2-Chloro-N-(3-chloro-phenyl)-acetamide | 4-Chlorobenzoyl chloride |
| 105 | D | 3-Chloro-benzylamine | 2-Chloro-N-(3-chloro-phenyl)-acetamide | 4-Chlorobenzoyl chloride |
| 106 | D | 2-Chloro-benzylamine | 2-Chloro-N-(3-chloro-phenyl)-acetamide | 4-Chlorobenzoyl chloride |
| 107 | D | C-Furan-2-yl-methylamine | 2-Chloro-N-(3-chloro-phenyl)-acetamide | 4-Chlorobenzoyl chloride |
| 108 | C | Phenylamino-acetic acid ethyl ester | 2-Bromo-N-(3,4-dichloro phenyl)-acetamide | 4-methoxy benzoyl chloride |
| 119 | B | 2-fluoro-benzylamine | 3-Chloro aniline | 6-Morpholin-4-yl-nicotinoyl chloride |
| 120 | B | 2-fluoro-benzylamine | 3-Chloro aniline | 6-Chloro-nicotinoyl chloride |
| 121 | B | 2-Fluoro-benzylamine | 3-Chloro aniline | 2-Chloro-isonicotinoyl chloride |
| 122 | B | 2-Fluoro-benzylamine | 3-Chloro aniline | 2,6-Dichloro-isonicotinoyl chloride |
| 123 | A | C-Cyclohexyl-methylamine | 2-Chloro-N-(3-chloro-phenyl)-acetamide | 4-chlorobenzoyl chloride |
| 124 | A | C-Cyclohexyl-methylamine | 2-Chloro-N-(3-chloro-phenyl)-acetamide | 4-Chlorobenzoyl chloride |
| 125 | A | C-Cyclohexyl-methylamine | 2-Chloro-N-(3-chloro-phenyl)-acetamide | 4-Fluorobenzoyl chloride |
| 126 | A | Cyclopentylamine | 2,4-Dichloro-N-(3-chloro-phenyl)-acetamide | 4-Methoxybenzoyl chloride |
| 127 | A | Cyclopropylamine | 2,4-Dichloro-N-(3-chloro-phenyl)-acetamide | 4-Methoxybenzoyl chloride |
| 128 | A | Cyclohexylamine | 2,4-Dichloro-N-(3-chloro-phenyl)-acetamide | 4-Methoxybenzoyl chloride |

The following compounds have been prepared in accordance with table 1:

TABLE 2

I

| Procedure | R¹ | R² | R³ | R⁴ | X | IC$_{50}$ | Exp |
|---|---|---|---|---|---|---|---|
| D | 4-Cl-phenyl | 2,6-diF-benzyl | H | 3-Cl-phenyl | bond | 0.052 | 1 |
| D | 4-Cl-phenyl | 3,4-diF-benzyl | H | 3-Cl-phenyl | bond | 0.265 | 2 |
| D | 4-Cl-phenyl | 3,5-diF-benzyl | H | 3-Cl-phenyl | bond | 0.184 | 3 |
| D | 4-Cl-phenyl | 2,3-diF-benzyl | H | 3-Cl-phenyl | bond | 0.074 | 4 |
| D | 4-Cl-phenyl | 2,4-diF-benzyl | H | 3-Cl-phenyl | bond | 0.16 | 5 |
| D | 4-Cl-phenyl | 2,5-diF-benzyl | H | 3-Cl-phenyl | bond | 0.165 | 6 |

TABLE 2-continued
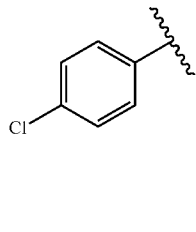
I
| Procedure | R¹ | R² | R³ | R⁴ | X | IC₅₀ | Exp |
|---|---|---|---|---|---|---|---|
| D | 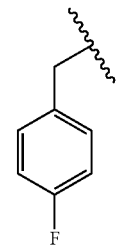 | 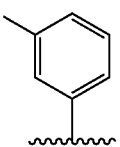 | H | 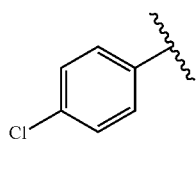 | bond | | 7 |
| D | 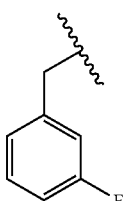 | 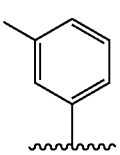 | H | 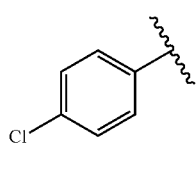 | bond | 0.128 | 8 |
| D | 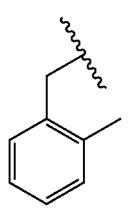 | 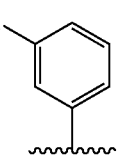 | H | 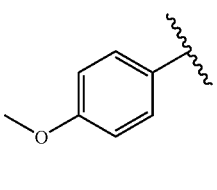 | bond | 0.074 | 9 |
| D | 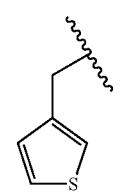 | 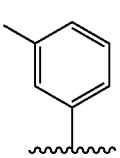 | H | 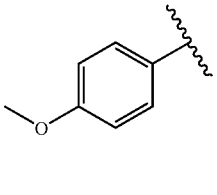 | bond | 0.285 | 10 |
| D | 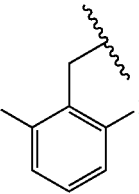 | 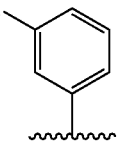 | H | 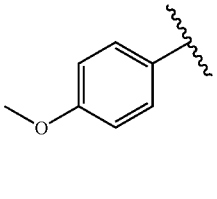 | bond | 0.1 | 11 |
| D | 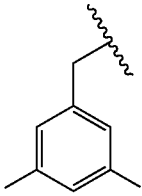 | 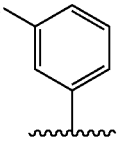 | H | | bond | 0.243 | 12 |

TABLE 2-continued
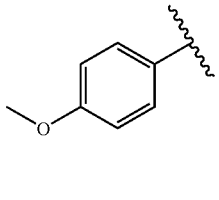
| Procedure | R¹ | R² | R³ | R⁴ | X | IC$_{50}$ | Exp |
|---|---|---|---|---|---|---|---|
| D | 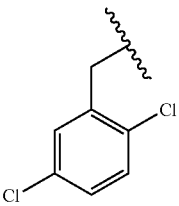 | 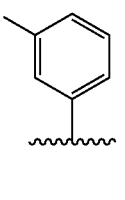 | H | 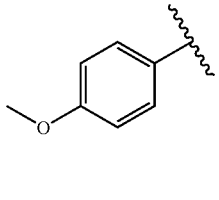 | bond | 0.122 | 13 |
| D | 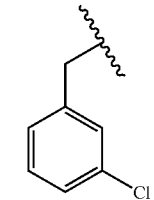 | 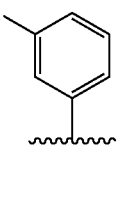 | H | 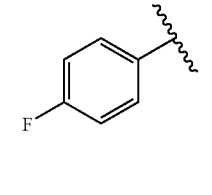 | bond | 0.024 | 14 |
| D | 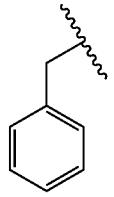 | 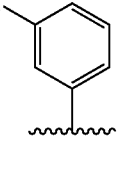 | H | 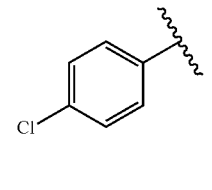 | bond | 0.312 | 15 |
| D | 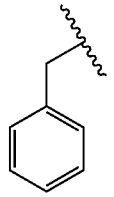 | 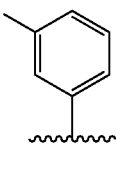 | H | 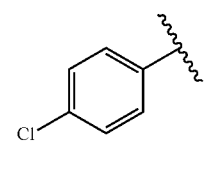 | bond | 0.156 | 16 |
| D | 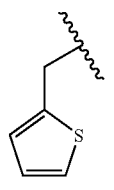 | 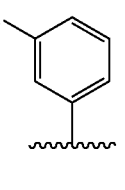 | H | 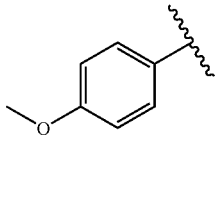 | bond | 0.077 | 17 |
| D | 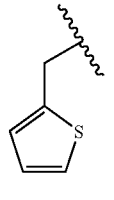 | 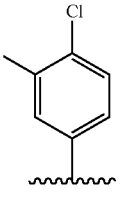 | H | | bond | 0.257 | 18 |

TABLE 2-continued

Structure I: R¹-X-C(=O)-N(R²)-CH₂-C(=O)-N(R³)(R⁴)

| Procedure | R¹ | R² | R³ | R⁴ | X | IC₅₀ | Exp |
|---|---|---|---|---|---|---|---|
| C | 4-methoxyphenyl | 2,6-dichlorobenzyl | H | 3-chlorophenyl | bond | 0.164 | 19 |
| D | 4-methoxyphenyl | 3-fluorophenyl | H | 3,4-dichlorophenyl | bond | | 20 |
| D | 4-methoxyphenyl | 2-fluorophenyl | H | 3,4-dichlorophenyl | bond | 0.315 | 21 |
| B | n-butyl | phenyl | H | 3,4-dichlorophenyl | bond | | 22 |
| C | 4-methoxyphenyl | phenyl | H | 4-chloro-3-fluorophenyl | bond | | 23 |
| C | 4-methoxyphenyl | phenyl | H | 2,2-difluorobenzo[1,3]dioxol-5-yl | bond | | 24 |
| C | 4-methoxyphenyl | phenyl | H | 3-(trifluoromethoxy)phenyl | bond | | 25 |

TABLE 2-continued

Structure I: R¹-X-N(R²)-C(O)-CH₂-N(R⁴)(R³) with C=O on the CH₂ side

| Procedure | R¹ | R² | R³ | R⁴ | X | IC₅₀ | Exp |
|---|---|---|---|---|---|---|---|
| C | 4-methoxyphenyl | phenyl | H | 3-methylphenyl | bond | | 26 |
| C | 4-methoxyphenyl | phenyl | H | 3-(trifluoromethyl)phenyl | bond | 0.148 | 27 |
| C | 4-methoxyphenyl | phenyl | H | 3-chlorophenyl | bond | 0.267 | 28 |
| C | 4-methoxyphenyl | phenyl | H | 3-methoxyphenyl | bond | | 29 |
| B | 3-(trifluoromethyl)phenyl | phenyl | H | 3,4-dichlorophenyl | bond | | 30 |
| B | 3-cyanophenyl | phenyl | H | 3,4-dichlorophenyl | bond | 0.35 | 31 |
| B | 2-methoxyphenyl | phenyl | H | 3,4-dichlorophenyl | bond | | 32 |

TABLE 2-continued

| Procedure | R¹ | R² | R³ | R⁴ | X | IC$_{50}$ | Exp |
|---|---|---|---|---|---|---|---|
| B | 3-methylphenyl | phenyl | H | 3,4-dichlorophenyl | bond | | 33 |
| A | 6-(trifluoromethyl)pyridin-3-yl | phenyl | H | 4-methylphenyl | bond | | 34 |
| B | 3-chlorophenyl | phenyl | H | 3,4-dichlorophenyl | bond | | 35 |
| A | 6-(trifluoromethyl)pyridin-3-yl | phenyl | H | 4-chlorophenyl | bond | | 36 |
| B | 6-(trifluoromethyl)pyridin-3-yl | phenyl | H | 3,4-dichlorophenyl | bond | 0.154 | 37 |
| B | 4-cyanophenyl | phenyl | H | 3,4-dichlorophenyl | bond | | 38 |
| B | 2-fluorophenyl | phenyl | H | 3,4-dichlorophenyl | bond | 0.291 | 39 |

TABLE 2-continued

I

| Procedure | R¹ | R² | R³ | R⁴ | X | IC₅₀ | Exp |
|---|---|---|---|---|---|---|---|
| B | 3-F-phenyl | phenyl | H | 3,4-diCl-phenyl | bond | | 40 |
| B | 4-MeO-phenyl | phenyl | H | 3,4-diCl-phenyl | bond | 0.276 | 41 |
| B | 4-F-phenyl | phenyl | H | 3,4-diCl-phenyl | bond | | 42 |
| D | 4-CN-phenyl | 2-Cl-benzyl | H | 3-CF₃-phenyl | bond | 0.339 | 43 |
| D | 3-CF₃-phenyl | 2-Cl-benzyl | H | 3-CF₃-phenyl | bond | | 44 |
| D | benzothiophen-2-yl | 3,5-diF-benzyl | H | 3-CF₃-phenyl | bond | 0.298 | 45 |

TABLE 2-continued

Structure I: R¹-X-C(=O)-N(R²)-CH₂-C(=O)-N(R⁴)(R³)

| Procedure | R¹ | R² | R³ | R⁴ | X | IC₅₀ | Exp |
|---|---|---|---|---|---|---|---|
| D | 3-fluorophenyl | 3,5-difluorobenzyl | H | 3-(trifluoromethyl)phenyl | bond | | 46 |
| D | 4-chlorophenyl | 3,5-difluorobenzyl | H | 3-(trifluoromethyl)phenyl | bond | | 47 |
| D | 4-(trifluoromethoxy)phenyl | 3,5-difluorobenzyl | H | 3-(trifluoromethyl)phenyl | bond | | 48 |
| D | 4-fluorophenyl | 3,5-difluorobenzyl | H | 3-(trifluoromethyl)phenyl | bond | | 49 |
| D | 4-cyanophenyl | 3,5-difluorobenzyl | H | 3-(trifluoromethyl)phenyl | bond | | 50 |
| D | benzothiophen-2-yl | 2-chlorobenzyl | H | 3-(trifluoromethyl)phenyl | bond | 0.06 | 51 |

TABLE 2-continued

Structure I: R¹-X-C(=O)-N(R²)-CH₂-C(=O)-N(R⁴)(R³)

| Procedure | R¹ | R² | R³ | R⁴ | X | IC$_{50}$ | Exp |
|---|---|---|---|---|---|---|---|
| D | 3-fluorophenyl | 2-chlorobenzyl | H | 3-(trifluoromethyl)phenyl | bond | 0.153 | 52 |
| D | 4-chlorophenyl | 2-chlorobenzyl | H | 3-(trifluoromethyl)phenyl | bond | 0.241 | 53 |
| D | 4-(trifluoromethoxy)phenyl | 2-chlorobenzyl | H | 3-(trifluoromethyl)phenyl | bond | 0.196 | 54 |
| D | 4-fluorophenyl | 2-chlorobenzyl | H | 3-(trifluoromethyl)phenyl | bond | 0.097 | 55 |
| D | 3-(trifluoromethyl)phenyl | 3,5-difluorobenzyl | H | 3-(trifluoromethyl)phenyl | bond | | 56 |
| D | benzothiophen-2-yl | 2-chlorobenzyl | H | 3-fluorophenyl | bond | 0.088 | 57 |

TABLE 2-continued
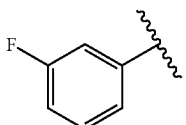
I
| Procedure | R¹ | R² | R³ | R⁴ | X | IC₅₀ | Exp |
|---|---|---|---|---|---|---|---|
| D | 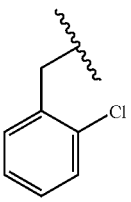 | 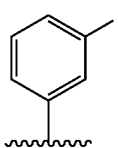 | H | 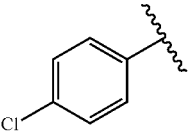 | bond | | 58 |
| D | 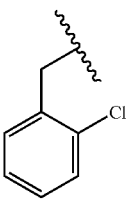 | 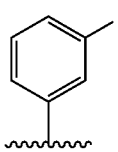 | H | 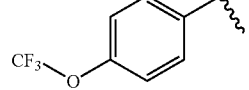 | bond | 0.166 | 59 |
| D | 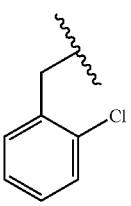 | 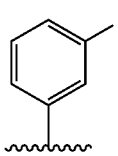 | H | 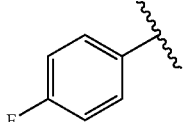 | bond | 0.107 | 60 |
| D | 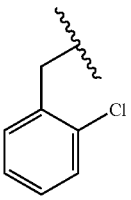 | 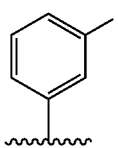 | H | 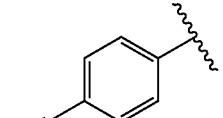 | bond | | 61 |
| D | 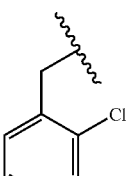 | 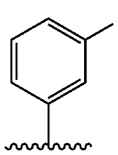 | H | 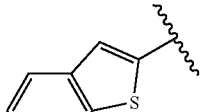 | bond | 0.357 | 62 |
| D | 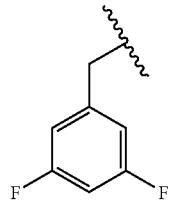 | 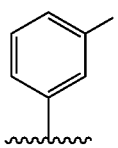 | H | | bond | 0.07 | 63 |

TABLE 2-continued
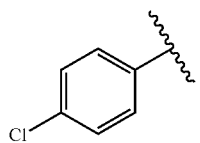
I
| Procedure | R¹ | R² | R³ | R⁴ | X | IC₅₀ | Exp |
|---|---|---|---|---|---|---|---|
| D | 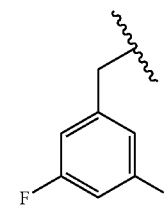 | 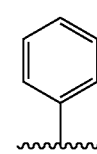 | H | 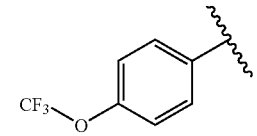 | bond | | 64 |
| D | 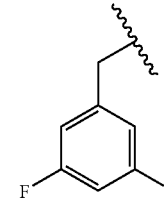 | 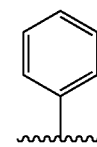 | H | 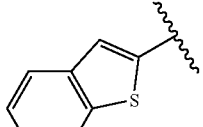 | bond | 0.278 | 65 |
| D | 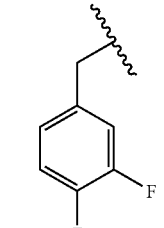 | 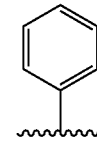 | H | 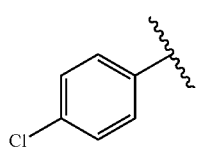 | bond | 0.167 | 66 |
| D | 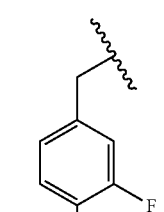 | 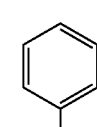 | H | 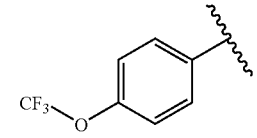 | bond | | 67 |
| D | 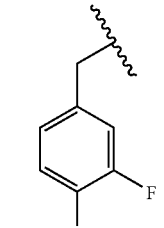 | 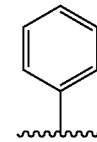 | H | 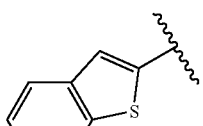 | bond | | 68 |
| D | 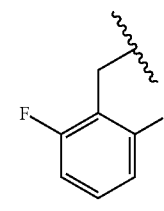 | 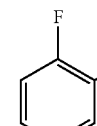 | H |  | bond | 0.09 | 69 |

TABLE 2-continued
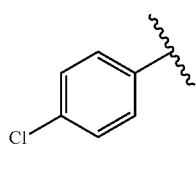
I
| Procedure | R$^1$ | R$^2$ | R$^3$ | R$^4$ | X | IC$_{50}$ | Exp |
|---|---|---|---|---|---|---|---|
| D | 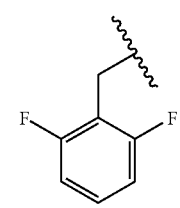 | 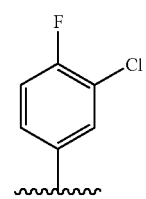 | H | 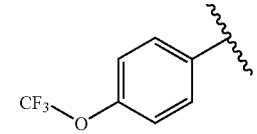 | bond |  | 70 |
| D | 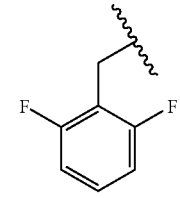 | 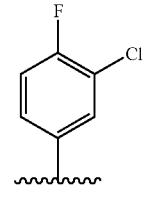 | H | 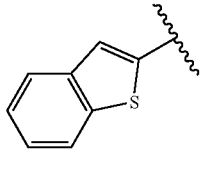 | bond | 0.107 | 71 |
| D | 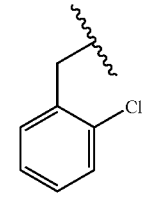 | 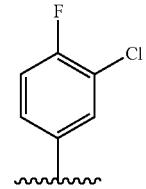 | H | 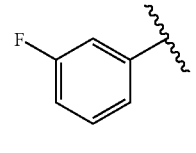 | bond | 0.205 | 72 |
| D | 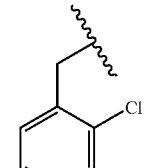 | 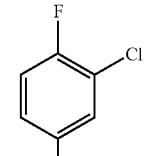 | H | 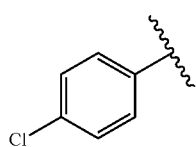 | bond |  | 73 |
| D | 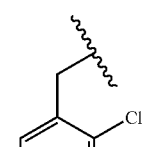 |  | H | 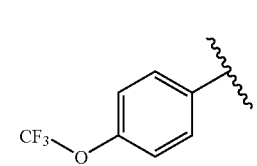 | bond | 0.142 | 74 |
| D | 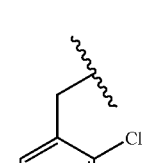 | 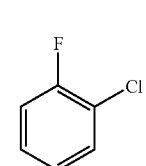 | H |  | bond | 0.259 | 75 |

TABLE 2-continued
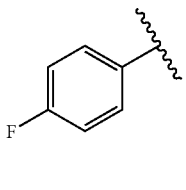
I
| Procedure | R¹ | R² | R³ | R⁴ | X | IC₅₀ | Exp |
|---|---|---|---|---|---|---|---|
| D | 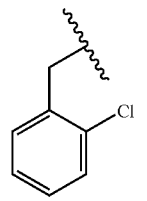 | 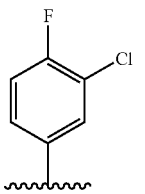 | H | 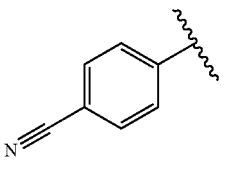 | bond | 0.159 | 76 |
| D | 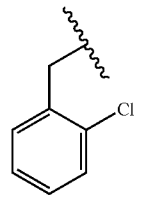 | 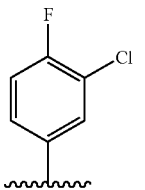 | H | 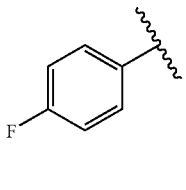 | bond | 0.182 | 77 |
| D | 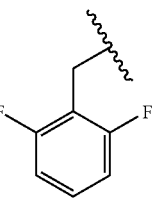 | 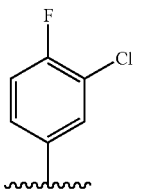 | H | 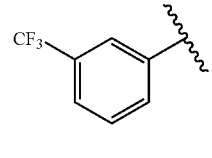 | bond | 0.282 | 78 |
| D | 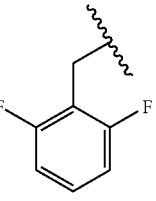 | 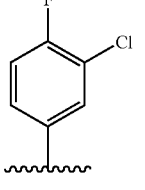 | H | 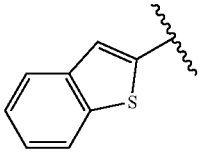 | bond |  | 79 |
| D | 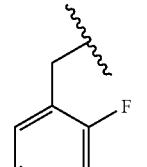 | 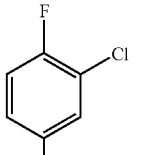 | H | 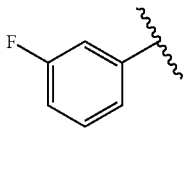 | bond | 0.066 | 80 |
| D | 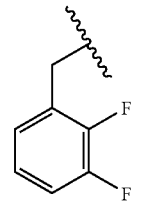 | 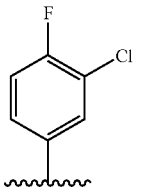 | H |  | bond |  | 81 |

TABLE 2-continued
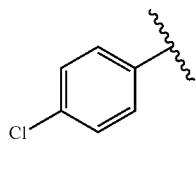
I
| Procedure | R¹ | R² | R³ | R⁴ | X | IC₅₀ | Exp |
|---|---|---|---|---|---|---|---|
| D | 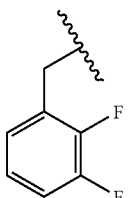 | 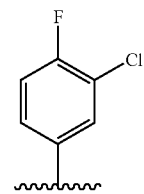 | H | 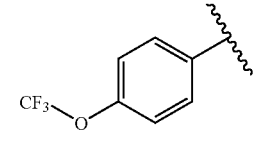 | bond | 0.108 | 82 |
| D | 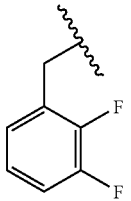 | 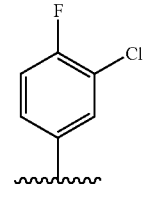 | H | 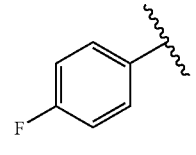 | bond | 0.078 | 83 |
| D | 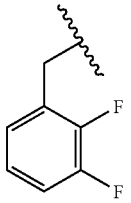 | 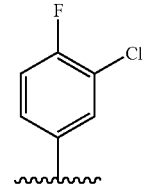 | H | 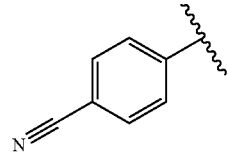 | bond | 0.178 | 84 |
| D | 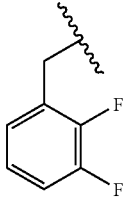 | 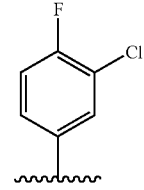 | H | 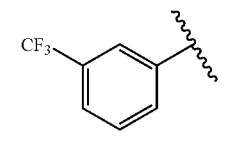 | bond | 0.123 | 85 |
| D | 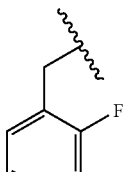 | 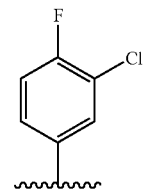 | H | 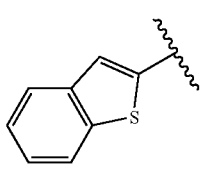 | bond | | 86 |
| D | 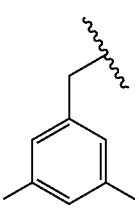 | 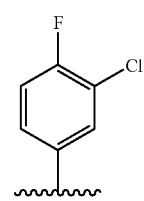 | H | | bond | 0.036 | 87 |

TABLE 2-continued
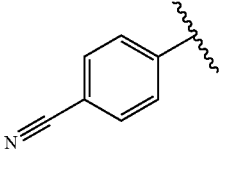
I
| Procedure | R¹ | R² | R³ | R⁴ | X | IC₅₀ | Exp |
|---|---|---|---|---|---|---|---|
| D | 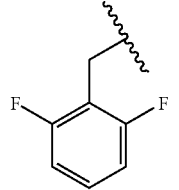 | 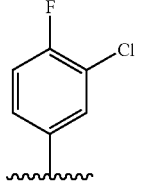 | H | 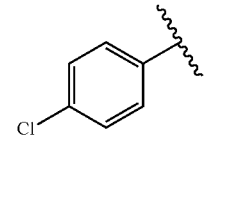 | bond | 0.199 | 88 |
| D | 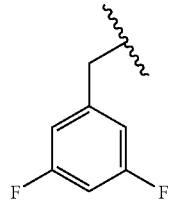 | 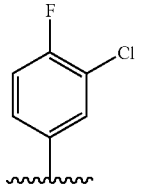 | H | 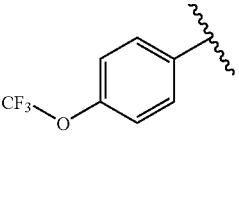 | bond | 0.306 | 89 |
| D | 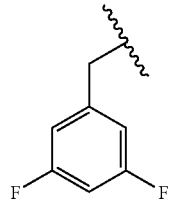 | 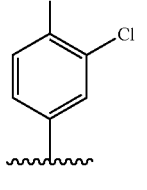 | H | 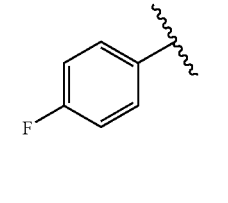 | bond | 0.288 | 90 |
| D | 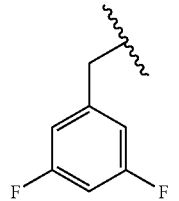 | 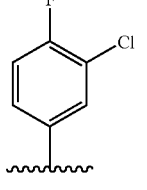 | H | 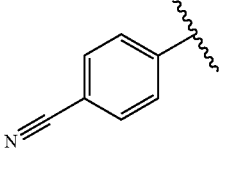 | bond |  | 91 |
| D | 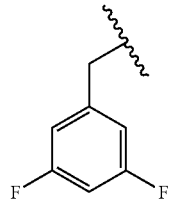 | 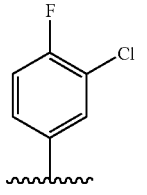 | H | 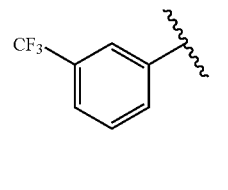 | bond |  | 92 |
| D | 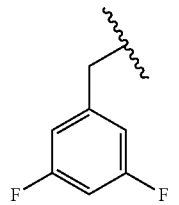 | 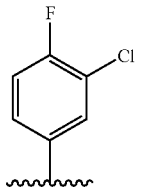 | H |  | bond |  | 93 |

TABLE 2-continued

Structure I:
R¹−X−C(=O)−N(R²)−CH₂−C(=O)−N(R³)(R⁴)

| Procedure | R¹ | R² | R³ | R⁴ | X | IC$_{50}$ | Exp |
|---|---|---|---|---|---|---|---|
| D | benzothiophen-2-yl | 3,4-difluorobenzyl | H | 3-chloro-4-fluorophenyl | bond | | 94 |
| D | 4-chlorophenyl | neopentyl | H | 3-chlorophenyl | bond | | 95 |
| D | 4-chlorophenyl | 3,3-dimethylbutyl | H | 3-chlorophenyl | bond | 0.359 | 96 |
| E | 4-methoxyphenyl | isobutyl | H | 3,4-dichlorophenyl | bond | | 97 |
| E | 4-methoxyphenyl | isopentyl | H | 3,4-dichlorophenyl | bond | | 98 |
| B | 4-methoxyphenyl | benzyl | H | 3,4-dichlorophenyl | bond | | 99 |

TABLE 2-continued

Structure I: R¹–X–N(R²)–C(O)–CH₂–C(O)–N(R³)(R⁴)

| Procedure | R¹ | R² | R³ | R⁴ | X | IC₅₀ | Exp |
|---|---|---|---|---|---|---|---|
| D | 4-Cl-phenyl | 3-cyanobenzyl | H | 3-Cl-phenyl | bond | 0.192 | 100 |
| D | 4-Cl-phenyl | 3-methoxybenzyl | H | 3-Cl-phenyl | bond | | 101 |
| D | 4-Cl-phenyl | 2-methoxybenzyl | H | 3-Cl-phenyl | bond | 0.06 | 102 |
| D | 4-Cl-phenyl | 3-methylbenzyl | H | 3-Cl-phenyl | bond | 0.142 | 103 |
| D | 4-Cl-phenyl | 2-methylbenzyl | H | 3-Cl-phenyl | bond | 0.209 | 104 |
| D | 4-Cl-phenyl | 3-Cl-benzyl | H | 3-Cl-phenyl | bond | 0.021 | 105 |

TABLE 2-continued
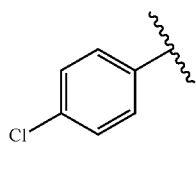
I
| Procedure | R¹ | R² | R³ | R⁴ | X | IC₅₀ | Exp |
|---|---|---|---|---|---|---|---|
| D | 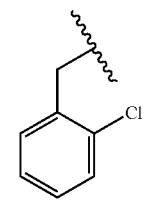 | 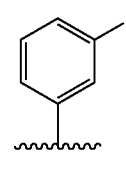 | H | 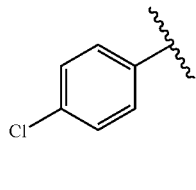 | bond | 0.025 | 106 |
| D | 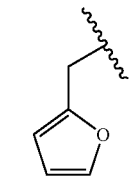 | 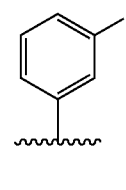 | H | 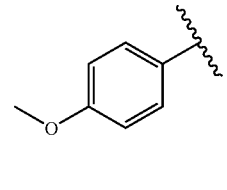 | bond | 0.199 | 107 |
| C | 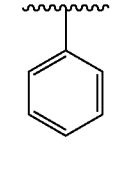 | 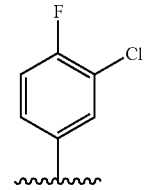 | H | 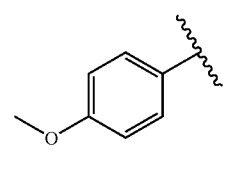 | bond | 0.182 | 108 |
| C | 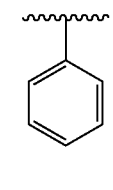 | 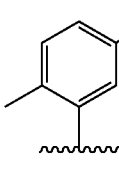 | H | 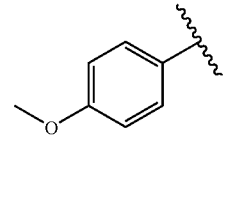 | bond | | 109 |
| C | 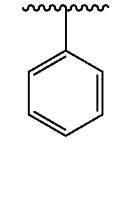 | 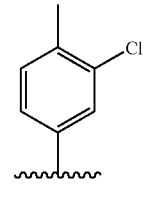 | H | 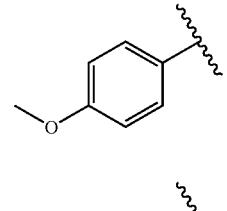 | bond | 0.369 | 110 |
| C | 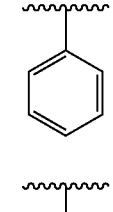 | 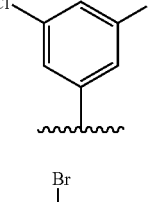 | H | 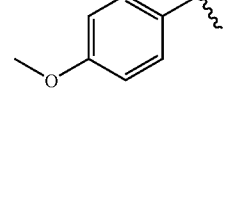 | bond | | 111 |
| C | 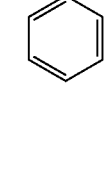 | 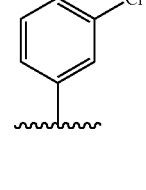 | H | | bond | | 112 |

TABLE 2-continued
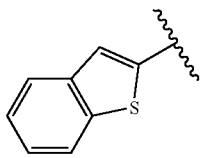
I
| Procedure | R¹ | R² | R³ | R⁴ | X | IC$_{50}$ | Exp |
|---|---|---|---|---|---|---|---|
| B | 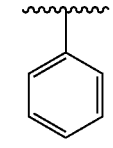 | 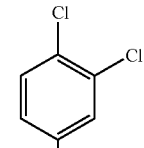 | H | 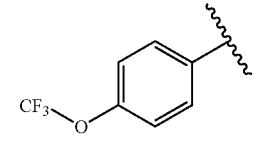 | bond | 0.15 | 113 |
| B | 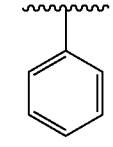 | 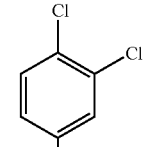 | H | 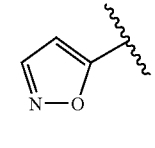 | bond | 0.091 | 114 |
| B | 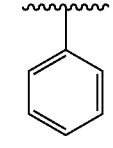 | 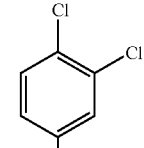 | H | 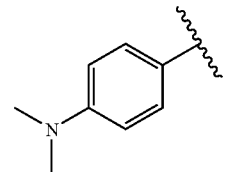 | bond | | 115 |
| B | 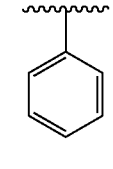 | 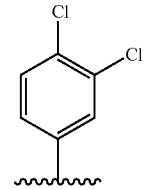 | H | 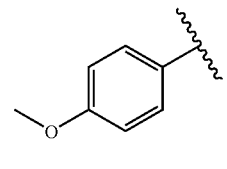 | bond | 0.191 | 116 |
| B | 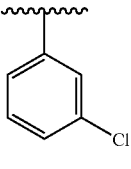 | 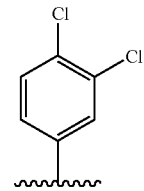 | H | 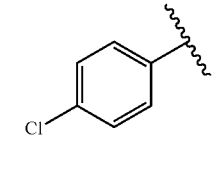 | bond | 0.21 | 117 |
| B | 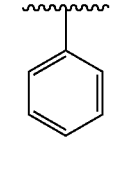 | 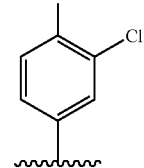 | H | 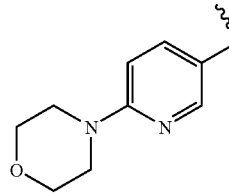 | OCH$_2$ | 0.259 | 118 |
| B | 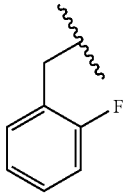 | 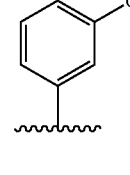 | H |  | bond | 0.355 | 119 |

TABLE 2-continued

Structure I: R¹-X-C(=O)-N(R²)-CH₂-C(=O)-N(R³)(R⁴)

| Procedure | R¹ | R² | R³ | R⁴ | X | IC₅₀ | Exp |
|---|---|---|---|---|---|---|---|
| B | 6-chloropyridin-3-yl | 2-chlorobenzyl | H | 3-chlorophenyl | bond | 0.182 | 120 |
| B | 2-chloropyridin-4-yl | 2-fluorobenzyl | H | 3-chlorophenyl | bond | | 121 |
| B | 2,6-dichloropyridin-4-yl | 2-fluorobenzyl | H | 3-chlorophenyl | bond | | 122 |
| A | 4-chlorophenyl | 3-fluorobenzyl | CH₃ | 3-chlorophenyl | bond | | 123 |
| A | 4-chlorophenyl | cyclohexylmethyl | H | 3-chlorophenyl | bond | | 124 |
| A | 4-fluorophenyl | cyclohexylmethyl | H | 3-chlorophenyl | bond | | 125 |

TABLE 2-continued

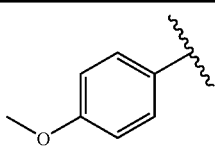

| Procedure | R¹ | R² | R³ | R⁴ | X | IC$_{50}$ | Exp |
|---|---|---|---|---|---|---|---|
| A | 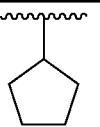 4-methoxyphenyl | cyclopentyl | H | 3,4-dichlorophenyl | bond | 0.357 | 126 |
| A | 4-methoxyphenyl | cyclopropyl | H | 3,4-dichlorophenyl | bond | | 127 |
| A | 4-methoxyphenyl | cyclohexyl | H | 3,4-dichlorophenyl | bond | | 128 |

TABLE 3

| Compound name | MW | MS result | MS mode | Example |
|---|---|---|---|---|
| 4-Chloro-N-[(3-chloro-phenylcarbamoyl)-methyl]-N-(2,6-difluoro-benzyl)-benzamide | 449.28 | 447.0 | neg | 1 |
| 4-Chloro-N-[(3-chloro-phenylcarbamoyl)-methyl]-N-(3,4-difluoro-benzyl)-benzamide | 449.28 | 447.0 | neg | 2 |
| 4-Chloro-N-[(3-chloro-phenylcarbamoyl)-methyl]-N-(3,5-difluoro-benzyl)-benzamide | 449.28 | 447.0 | neg | 3 |
| 4-Chloro-N-[(3-chloro-phenylcarbamoyl)-methyl]-N-(2,3-difluoro-benzyl)-benzamide | 449.28 | 449.2 | pos | 4 |
| 4-Chloro-N-[(3-chloro-phenylcarbamoyl)-methyl]-N-(2,4-difluoro-benzyl)-benzamide | 449.28 | 449.2 | pos | 5 |
| 4-Chloro-N-[(3-chloro-phenylcarbamoyl)-methyl]-N-(2,5-difluoro-benzyl)-benzamide | 449.28 | 449.2 | pos | 6 |
| 4-Chloro-N-[(3-chloro-phenylcarbamoyl)-methyl]-N-(4-fluoro-benzyl)-benzamide | 431.29 | 431.4 | pos | 7 |
| 4-Chloro-N-[(3-chloro-phenylcarbamoyl)-methyl]-N-(3-fluoro-benzyl)-benzamide | 431.29 | 431.4 | pos | 8 |
| 4-Chloro-N-[(3-chloro-phenylcarbamoyl)-methyl]-N-(2-fluoro-benzyl)-benzamide | 431.29 | 431.4 | pos | 9 |
| N-[(3-Chloro-phenylcarbamoyl)-methyl]-4-methoxy-N-thiophen-3-ylmethyl-benzamide | 414.9 | 415.3 | pos | 10 |
| N-[(3-Chloro-phenylcarbamoyl)-methyl]-N-(2,6-difluoro-benzyl)-4-methoxy-benzamide | 444.9 | 443.2 | neg | 11 |
| N-[(3-Chloro-phenylcarbamoyl)-methyl]-N-(3,5-dichloro-benzyl)-4-methoxy-benzamide | 477.8 | 477.1 | pos | 12 |
| N-[(3-Chloro-phenylcarbamoyl)-methyl]-N-(2,5-dichloro-benzyl)-4-methoxy-benzamide | 477.8 | 479.2 | pos | 13 |
| N-(3-Chloro-benzyl)-N-[(3-chloro-phenylcarbamoyl)-methyl]-4-methoxy-benzamide | 443.3 | 443.3 | pos | 14 |
| N-Benzyl-N-[(3-chloro-phenylcarbamoyl)-methyl]-4-fluoro-benzamide | 496.8 | 497.1 | pos | 15 |
| N-Benzyl-4-chloro-N-[(3-chloro-phenylcarbamoyl)-methyl]-benzamide | 413.3 | 413.2 | pos | 16 |

TABLE 3-continued

| Compound name | MW | MS result | MS mode | Example |
|---|---|---|---|---|
| 4-Chloro-N-[(3-chloro-phenylcarbamoyl)-methyl]-N-thiophen-2-ylmethyl-benzamide | 419.3 | 419.1 | pos | 17 |
| N-[(3,4-Dichloro-phenylcarbamoyl)-methyl]-4-methoxy-N-thiophen-2-ylmethyl-benzamide | 449.4 | 449.1 | pos | 18 |
| N-[(3-Chloro-phenylcarbamoyl)-methyl]-N-(2,6-dichloro-benzyl)-4-methoxy-benzamide | 477.8 | 479.2 | pos | 19 |
| N-[(3,4-Dichloro-phenylcarbamoyl)-methyl]-N-(3-fluoro-phenyl)-4-methoxy-benzamide | 447.3 | 447.1 | pos | 20 |
| N-[(3,4-Dichloro-phenylcarbamoyl)-methyl]-N-(2-fluoro-phenyl)-4-methoxy-benzamide | 447.3 | 447.1 | pos | 21 |
| Pentanoic acid [(3,4-dichloro-phenylcarbamoyl)-methyl]-phenyl-amide | 379.3 | 379.3 | pos | 22 |
| N-[(3-Chloro-2-fluoro-phenylcarbamoyl)-methyl]-4-methoxy-N-phenyl-benzamide | 412.8 | 413.4 | pos | 23 |
| N-[(2,2-Difluoro-benzo[1,3]dioxol-5-ylcarbamoyl)-methyl]-4-methoxy-N-phenyl-benzamide | 440.4 | 441.0 | pos | 24 |
| 4-Methoxy-N-phenyl-N-[(3-trifluoromethoxy-phenylcarbamoyl)-methyl]-benzamide | 444.4 | 445.1 | pos | 25 |
| 4-Methoxy-N-phenyl-N-(m-tolylcarbamoyl-methyl)-benzamide | 374.4 | 375.1 | pos | 26 |
| 4-Methoxy-N-phenyl-N-[(3-trifluoromethyl-phenylcarbamoyl)-methyl]-benzamide | 428.4 | 429.0 | pos | 27 |
| N-[(3-Chloro-phenylcarbamoyl)-methyl]-4-methoxy-N-phenyl-benzamide | 394.9 | 395.0 | pos | 28 |
| 4-Methoxy-N-[(3-methoxy-phenylcarbamoyl)-methyl]-N-phenyl-benzamide | 390.4 | 391.3 | pos | 29 |
| N-[(3,4-Dichloro-phenylcarbamoyl)-methyl]-N-phenyl-3-trifluoromethyl-benzamide | 467.3 | 467.0 | pos | 30 |
| 3-Cyano-N-[(3,4-dichloro-phenylcarbamoyl)-methyl]-N-phenyl-benzamide | 424.3 | 467.0 | pos | 31 |
| N-[(3,4-Dichloro-phenylcarbamoyl)-methyl]-2-methoxy-N-phenyl-benzamide | 429.3 | 429.2 | pos | 32 |
| N-[(3,4-Dichloro-phenylcarbamoyl)-methyl]-3-methyl-N-phenyl-benzamide | 413.3 | 413.2 | pos | 33 |
| N-Phenyl-N-(p-tolylcarbamoyl-methyl)-6-trifluoromethyl-nicotinamide | 413.4 | 414.4 | pos | 34 |
| 3-Chloro-N-[(3,4-dichloro-phenylcarbamoyl)-methyl]-N-phenyl-benzamide | 433.7 | 433.0 | pos | 35 |
| N-[(4-Fluoro-phenylcarbamoyl)-methyl]-N-phenyl-6-trifluoromethyl-nicotinamide | 417.4 | 418.0 | pos | 36 |
| N-[(3,4-Dichloro-phenylcarbamoyl)-methyl]-N-phenyl-6-trifluoromethyl-nicotinamide | 468.3 | 468.1 | pos | 37 |
| 4-Cyano-N-[(3,4-dichloro-phenylcarbamoyl)-methyl]-N-phenyl-benzamide | 424.3 | 424.0 | pos | 38 |
| N-[(3,4-Dichloro-phenylcarbamoyl)-methyl]-2-fluoro-N-phenyl-benzamide | 417.3 | 417.3 | pos | 39 |
| N-[(3,4-Dichloro-phenylcarbamoyl)-methyl]-3-fluoro-N-phenyl-benzamide | 417.3 | 417.1 | pos | 40 |
| N-[(3,4-Dichloro-phenylcarbamoyl)-methyl]-4-methoxy-N-phenyl-benzamide | 429.3 | 429.3 | pos | 41 |
| N-[(3,4-Dichloro-phenylcarbamoyl)-methyl]-4-fluoro-N-phenyl-benzamide | 417.3 | 417.1 | pos | 42 |
| N-(2-Chloro-benzyl)-4-cyano-N-[(3-trifluoromethyl-phenylcarbamoyl)-methyl]-benzamide | 471.9 | 472.2 | pos | 43 |
| N-(2-Chloro-benzyl)-3-trifluoromethyl-N-[(3-trifluoromethyl-phenylcarbamoyl)-methyl]-benzamide | 514.9 | 515.2 | pos | 44 |
| Benzo[b]thiophene-2-carboxylic acid (3,5-difluoro-benzyl)-[(3-trifluoromethyl-phenylcarbamoyl)-methyl]-amide | 504.5 | 506.2 | pos | 45 |
| N-(3,5-Difluoro-benzyl)-3-fluoro-N-[(3-trifluoromethyl-phenylcarbamoyl)-methyl]-benzamide | 466.4 | 467.2 | pos | 46 |
| 4-Chloro-N-(3,5-difluoro-benzyl)-N-[(3-trifluoromethyl-phenylcarbamoyl)-methyl]-benzamide | 482.8 | 483.4 | pos | 47 |
| N-(3,5-Difluoro-benzyl)-4-trifluoromethoxy-N-[(3-trifluoromethyl-phenylcarbamoyl)-methyl]-benzamide | 432.4 | 433.2 | pos | 48 |
| N-(3,5-Difluoro-benzyl)-4-fluoro-N-[(3-trifluoromethyl-phenylcarbamoyl)-methyl]-benzamide | 466.4 | 467.2 | pos | 49 |
| 4-Cyano-N-(3,5-difluoro-benzyl)-N-[(3-trifluoromethyl-phenylcarbamoyl)-methyl]-benzamide | 473.4 | 474.2 | pos | 50 |

TABLE 3-continued

| Compound name | MW | MS result | MS mode | Example |
|---|---|---|---|---|
| Benzo[b]thiophene-2-carboxylic acid (2-chloro-benzyl)-[(3-trifluoromethyl-phenylcarbamoyl)-methyl]-amide | 502.9 | 503.1 | pos | 51 |
| N-(2-Chloro-benzyl)-3-fluoro-N-[(3-trifluoromethyl-phenylcarbamoyl)-methyl]-benzamide | 464.9 | 465.3 | pos | 52 |
| 4-Chloro-N-(2-chloro-benzyl)-N-[(3-trifluoromethyl-phenylcarbamoyl)-methyl]-benzamide | 481.3 | 481.2 | pos | 53 |
| #N!-(2-Chloro-benzyl)-4-trifluoromethoxy-#N!-[(3-trifluoromethyl-phenylcarbamoyl)-methyl]-benzamide | 530.9 | 531.1 | pos | 54 |
| N-(2-Chloro-benzyl)-4-fluoro-N-[(3-trifluoromethyl-phenylcarbamoyl)-methyl]-benzamide | 464.9 | 465.3 | pos | 55 |
| N-(3,5-Difluoro-benzyl)-3-trifluoromethyl-N-[(3-trifluoromethyl-phenylcarbamoyl)-methyl]-benzamide | 516.4 | 517.2 | pos | 56 |
| Benzo[b]thiophene-2-carboxylic acid (2-chloro-benzyl)-[(3-fluoro-phenylcarbamoyl)-methyl]-amide | 452.9 | 453.0 | pos | 57 |
| N-(2-Chloro-benzyl)-3-fluoro-N-[(3-fluoro-phenylcarbamoyl)-methyl]-benzamide | 414.8 | 415.3 | pos | 58 |
| 4-Chloro-N-(2-chloro-benzyl)-N-[(3-fluoro-phenylcarbamoyl)-methyl]-benzamide | 431.3 | 431.1 | pos | 59 |
| N-(2-Chloro-benzyl)-N-[(3-fluoro-phenylcarbamoyl)-methyl]-4-trifluoromethoxy-benzamide | 480.8 | 481.1 | pos | 60 |
| N-(2-Chloro-benzyl)-4-fluoro-N-[(3-fluoro-phenylcarbamoyl)-methyl]-benzamide | 414.8 | 415.2 | pos | 61 |
| N-(2-Chloro-benzyl)-4-cyano-N-[(3-fluoro-phenylcarbamoyl)-methyl]-benzamide | 421.9 | 422.1 | pos | 62 |
| Benzo[b]thiophene-2-carboxylic acid (3,5-difluoro-benzyl)-[(3-fluoro-phenylcarbamoyl)-methyl]-amide | 454.5 | 455.2 | pos | 63 |
| 4-Chloro-N-(3,5-difluoro-benzyl)-N-[(3-fluoro-phenylcarbamoyl)-methyl]-benzamide | 432.8 | 433.2 | pos | 64 |
| N-(3,5-Difluoro-benzyl)-N-[(3-fluoro-phenylcarbamoyl)-methyl]-4-trifluoromethoxy-benzamide | 482.4 | 483.1 | pos | 65 |
| Benzo[b]thiophene-2-carboxylic acid (3,4-difluoro-benzyl)-[(3-fluoro-phenylcarbamoyl)-methyl]-amide | 454.5 | 455.2 | pos | 66 |
| 4-Chloro-N-(3,4-difluoro-benzyl)-N-[(3-fluoro-phenylcarbamoyl)-methyl]-benzamide | 432.8 | 433.2 | pos | 67 |
| N-(3,4-Difluoro-benzyl)-N-[(3-fluoro-phenylcarbamoyl)-methyl]-4-trifluoromethoxy-benzamide | 482.4 | 483.4 | pos | 68 |
| Benzo[b]thiophene-2-carboxylic acid [(3-chloro-4-fluoro-phenylcarbamoyl)-methyl]-(2,6-difluoro-benzyl)-amide | 488.9 | 489.1 | pos | 69 |
| 4-Chloro-N-[(3-chloro-4-fluoro-phenylcarbamoyl)-methyl]-N-(2,6-difluoro-benzyl)-benzamide | 467.3 | 467.1 | pos | 70 |
| N-[(3-Chloro-4-fluoro-phenylcarbamoyl)-methyl]-N-(2,6-difluoro-benzyl)-4-trifluoromethoxy-benzamide | 518.8 | 517.1 | pos | 71 |
| Benzo[b]thiophene-2-carboxylic acid (2-chloro-benzyl)-[(3-chloro-4-fluoro-phenylcarbamoyl)-methyl]-amide | 487.4 | 487.2 | pos | 72 |
| N!-(2-Chloro-benzyl)-N!-[(3-chloro-4-fluoro-phenylcarbamoyl)-methyl]-3-fluoro-benzamide | 449.3 | 449.1 | pos | 73 |
| 4-Chloro-N-(2-chloro-benzyl)-N-[(3-chloro-4-fluoro-phenylcarbamoyl)-methyl]-benzamide | 465.7 | 465.2 | pos | 74 |
| N-(2-Chloro-benzyl)-N-[(3-chloro-4-fluoro-phenylcarbamoyl)-methyl]-4-trifluoromethoxy-benzamide | 515.3 | 512.3 | pos | 75 |
| N-(2-Chloro-benzyl)-N-[(3-chloro-4-fluoro-phenylcarbamoyl)-methyl]-4-fluoro-benzamide | 449.3 | 449.1 | pos | 76 |
| N-(2-Chloro-benzyl)-N-[(3-chloro-4-fluoro-phenylcarbamoyl)-methyl]-4-cyano-benzamide | 456.3 | 456.3 | pos | 77 |
| N-[(3-Chloro-4-fluoro-phenylcarbamoyl)-methyl]-N-(2,6-difluoro-benzyl)-4-fluoro-benzamide | 450.8 | 451.1 | pos | 78 |
| N-(2-Chloro-benzyl)-N-[(3-chloro-4-fluoro-phenylcarbamoyl)-methyl]-3-trifluoromethyl-benzamide | 499.3 | 499.2 | pos | 79 |
| Benzo[b]thiophene-2-carboxylic acid [(3-chloro-4-fluoro-phenylcarbamoyl)-methyl]-(2,3-difluoro-benzyl)-amide | 488.9 | 489.2 | pos | 80 |

TABLE 3-continued

| Compound name | MW | MS result | MS mode | Example |
|---|---|---|---|---|
| N-[(3-Chloro-4-fluoro-phenylcarbamoyl)-methyl]-N-(2,3-difluoro-benzyl)-3-fluoro-benzamide | 450.8 | 451.1 | pos | 81 |
| 4-Chloro-N-[(3-chloro-4-fluoro-phenylcarbamoyl)-methyl]-N-(2,3-difluoro-benzyl)-benzamide | 467.3 | 467.2 | pos | 82 |
| N-[(3-Chloro-4-fluoro-phenylcarbamoyl)-methyl]-N-(2,3-difluoro-benzyl)-4-trifluoromethoxy-benzamide | 516.8 | 517.1 | pos | 83 |
| N-[(3-Chloro-4-fluoro-phenylcarbamoyl)-methyl]-N-(2,3-difluoro-benzyl)-4-fluoro-benzamide | 450.8 | 451.1 | pos | 84 |
| N-[(3-Chloro-4-fluoro-phenylcarbamoyl)-methyl]-4-cyano-N-(2,3-difluoro-benzyl)-benzamide | 457.8 | 458.3 | pos | 85 |
| N-[(3-Chloro-4-fluoro-phenylcarbamoyl)-methyl]-N-(2,3-difluoro-benzyl)-3-trifluoromethyl-benzamide | 500.8 | 501.1 | pos | 86 |
| Benzo[b]thiophene-2-carboxylic acid [(3-chloro-4-fluoro-phenylcarbamoyl)-methyl]-(3,5-difluoro-benzyl)-amide | 488.9 | 499.1 | pos | 87 |
| N-[(3-Chloro-4-fluoro-phenylcarbamoyl)-methyl]-4-cyano-N-(2,6-difluoro-benzyl)-benzamide | 457.8 | 458.3 | pos | 88 |
| 4-Chloro-N-[(3-chloro-4-fluoro-phenylcarbamoyl)-methyl]-N-(3,5-difluoro-benzyl)-benzamide | 467.3 | 467.4 | pos | 89 |
| N-[(3-Chloro-4-fluoro-phenylcarbamoyl)-methyl]-N-(3,5-difluoro-benzyl)-4-trifluoromethoxy-benzamide | 516.8 | 517.1 | pos | 90 |
| N-[(3-Chloro-4-fluoro-phenylcarbamoyl)-methyl]-N-(3,5-difluoro-benzyl)-4-fluoro-benzamide | 450.8 | 451.1 | pos | 91 |
| N-[(3-Chloro-4-fluoro-phenylcarbamoyl)-methyl]-4-cyano-N-(3,5-difluoro-benzyl)-benzamide | 457.8 | 458.3 | pos | 92 |
| N-[(3-Chloro-4-fluoro-phenylcarbamoyl)-methyl]-N-(3,5-difluoro-benzyl)-3-trifluoromethyl-benzamide | 500.8 | 501.1 | pos | 93 |
| Benzo[b]thiophene-2-carboxylic acid [(3-chloro-4-fluoro-phenylcarbamoyl)-methyl]-(3,4-difluoro-benzyl)-amide | 488.9 | 489.1 | pos | 94 |
| 4-Chloro-N-[(3-chloro-phenylcarbamoyl)-methyl]-N-(2,2-dimethyl-propyl)-benzamide | 393.3 | 393.1 | neg | 95 |
| 4-Chloro-N-[(3-chloro-phenylcarbamoyl)-methyl]-N-(3,3-dimethyl-butyl)-benzamide | 407.3 | 408.3 | neg | 96 |
| N-[(3,4-Dichloro-phenylcarbamoyl)-methyl]-N-isobutyl-4-methoxy-benzamide | 409.3 | 409.2 | neg | 97 |
| N-[(3,4-Dichloro-phenylcarbamoyl)-methyl]-4-methoxy-N-(3-methyl-butyl)-benzamide | 423.3 | 421.0 | neg | 98 |
| N-Benzyl-N-[(3,4-dichloro-phenylcarbamoyl)-methyl]-4-methoxy-benzamide | 443.3 | 441.2 | neg | 99 |
| 4-Chloro-N-[(3-chloro-phenylcarbamoyl)-methyl]-N-(3-cyano-benzyl)-benzamide | 438.3 | 436.0 | neg | 100 |
| 4-Chloro-N-[(3-chloro-phenylcarbamoyl)-methyl]-N-(3-methoxy-benzyl)-benzamide | 443.3 | 440.9 | neg | 101 |
| 4-Chloro-N-[(3-chloro-phenylcarbamoyl)-methyl]-N-(2-methoxy-benzyl)-benzamide | 443.3 | 440.9 | neg | 102 |
| 4-Chloro-N-[(3-chloro-phenylcarbamoyl)-methyl]-N-(3-methyl-benzyl)-benzamide | 427.3 | 446.8 | neg | 103 |
| 4-Chloro-N-[(3-chloro-phenylcarbamoyl)-methyl]-N-(2-methyl-benzyl)-benzamide | 427.3 | 424.9 | neg | 104 |
| 4-Chloro-N-(3-chloro-benzyl)-N-[(3-chloro-phenylcarbamoyl)-methyl]-benzamide | 447.8 | 446.8 | neg | 105 |
| 4-Chloro-N-(2-chloro-benzyl)-N-[(3-chloro-phenylcarbamoyl)-methyl]-benzamide | 447.8 | 446.8 | neg | 106 |
| 4-Chloro-N-[(3-chloro-phenylcarbamoyl)-methyl]-N-furan-2-ylmethyl-benzamide | 403.3 | 401.0 | neg | 107 |
| N-[(3-Chloro-4-fluoro-phenylcarbamoyl)-methyl]-4-methoxy-N-phenyl-benzamide | 412.9 | 413.0 | pos | 108 |
| N-[(5-Chloro-2-methyl-phenylcarbamoyl)-methyl]-4-methoxy-N-phenyl-benzamide | 408.9 | 409.2 | pos | 109 |
| N-[(3-Chloro-4-methyl-phenylcarbamoyl)-methyl]-4-methoxy-N-phenyl-benzamide | 408.9 | 409.2 | pos | 110 |
| N-[(3,5-Dichloro-phenylcarbamoyl)-methyl]-4-methoxy-N-phenyl-benzamide | 429.3 | 429.3 | pos | 111 |
| N-[(4-Bromo-3-chloro-phenylcarbamoyl)-methyl]-4-methoxy-N-phenyl-benzamide | 473.8 | 472.9 | pos | 112 |
| Benzo[b]thiophene-2-carboxylic acid [(3,4-dichloro-phenylcarbamoyl)-methyl]-phenyl-amide | 455.4 | 454.9 | pos | 113 |
| N-[(3,4-Dichloro-phenylcarbamoyl)-methyl]-N-phenyl-4-trifluoromethoxy-benzamide | 483.3 | 482.9 | pos | 114 |
| Isoxazole-5-carboxylic acid [(3,4-dichloro-phenylcarbamoyl)-methyl]-phenyl-amide | 390.2 | 390.0 | pos | 115 |

TABLE 3-continued

| Compound name | MW | MS result | MS mode | Example |
|---|---|---|---|---|
| N-[(3,4-Dichloro-phenylcarbamoyl)-methyl]-4-dimethylamino-N-phenyl-benzamide | 442.3 | 442.0 | pos | 116 |
| N-(3-Chloro-phenyl)-N-[(3,4-dichloro-phenylcarbamoyl)-methyl]-4-methoxy-benzamide | 463.7 | 462.8 | pos | 117 |
| 2-(4-Chloro-phenoxy)-N-[(3,4-dichloro-phenylcarbamoyl)-methyl]-N-phenyl-acetamide | 463.7 | 462.8 | pos | 118 |
| N-[(3-Chloro-phenylcarbamoyl)-methyl]-N-(2-fluoro-benzyl)-6-morpholin-4-yl-nicotinamide | 462.9 | 483.5 | pos | 119 |
| 6-Chloro-N-[(3-chloro-phenylcarbamoyl)-methyl]-N-(2-fluoro-benzyl)-nicotinamide | 432.3 | 432.2 | pos | 120 |
| 2-Chloro-N-[(3-chloro-phenylcarbamoyl)-methyl]-N-(2-fluoro-benzyl)-isonicotinamide | 432.3 | 432.1 | pos | 121 |
| 2,6-Dichloro-N-[(3-chloro-phenylcarbamoyl)-methyl]-N-(2-fluoro-benzyl)-isonicotinamide | 466.7 | 468.1 | pos | 122 |
| 4-Chloro-N-{[(3-chloro-phenyl)-methyl-carbamoyl]-methyl}-N-(3-fluoro-benzyl)-benzamide | 445.3 | 445.4 | pos | 123 |
| 4-Chloro-N-[(3-chloro-phenylcarbamoyl)-methyl]-N-cyclohexylmethyl-benzamide | 419.4 | 419.1 | pos | 124 |
| N-[(3-Chloro-phenylcarbamoyl)-methyl]-N-cyclohexylmethyl-4-fluoro-benzamide | 402.9 | 403.3 | pos | 125 |
| N-Cyclopentyl-N-[(3,4-dichloro-phenylcarbamoyl)-methyl]-4-methoxy-benzamide | 421.3 | 420.9 | pos | 126 |
| N-Cyclopropyl-N-[(3,4-dichloro-phenylcarbamoyl)-methyl]-4-methoxy-benzamide | 393.3 | 393.0 | pos | 127 |
| N-Cyclohexyl-N-[(3,4-dichloro-phenylcarbamoyl)-methyl]-4-methoxy-benzamide | 435.3 | 435.1 | pos | 128 |

What is claimed is:

1. A compound of formula I

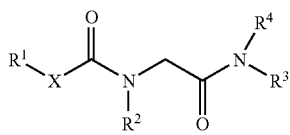

wherein
- $R^1$ is heteroaryl, which is optionally substituted by halogen, lower alkyl, lower alkoxy, lower alkyl substituted by halogen, lower alkoxy substituted by halogen, cyano, amino, di-lower alkyl amino or morpholinyl;
- $R^2$ is —$(CH_2)_n$-aryl, or —$(CH_2)_n$-heteroaryl wherein the aryl or heteroaryl groups are substituted by one or more substituents selected from the group consisting of halogen, lower alkyl, cyano, and lower alkoxy;
- $R^3$ is hydrogen or lower alkyl;
- $R^4$ is aryl or heteroaryl, wherein aryl and heteroaryl are optionally substituted by one or more substituents selected from the group consisting of halogen, lower alkyl substituted by halogen, lower alkoxy substituted by halogen, and lower alkyl;
- X is a bond or —$OCH_2$—; and
- n is 0, 1 or 2;

or a pharmaceutically acceptable acid addition salt thereof.

2. A compound of claim 1, wherein X is a bond.

3. A compound of claim 1, wherein $R^4$ is monosubstituted aryl.

4. A compound of claim 3, wherein the monosubstituted aryl is halogen substituted phenyl.

5. A compound of claim 1, wherein $R^1$ is heteroaryl.

6. A compound of claim 5, wherein $R^1$ is benzothiophenyl.

7. A compound of claim 6, selected from the group consisting of
- Benzo[b]thiophene-2-carboxylic acid (2-chloro-benzyl)-[(3-trifluoromethyl-phenylcarbamoyl)-methyl]-amide,
- Benzo[b]thiophene-2-carboxylic acid (2-chloro-benzyl)-[(3-fluoro-phenylcarbamoyl)-methyl]-amide,
- Benzo[b]thiophene-2-carboxylic acid (3,5-difluoro-benzyl)-[(3-fluoro-phenylcarbamoyl)-methyl]-amide,
- Benzo[b]thiophene-2-carboxylic acid [(3-chloro-4-fluoro-phenylcarbamoyl)-methyl]-(2,6-difluoro-benzyl)-amide,
- Benzo[b]thiophene-2-carboxylic acid [(3-chloro-4-fluoro-phenylcarbamoyl)-methyl]-(2,3-difluoro-benzyl)-amide and
- Benzo[b]thiophene-2-carboxylic acid [(3-chloro-4-fluoro-phenylcarbamoyl)-methyl]-(3,5-difluoro-benzyl)-amide.

8. A pharmaceutical composition comprising a compound of formula I

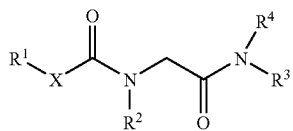

wherein
- $R^1$ is heteroaryl, which is optionally substituted by halogen, lower alkyl, lower alkoxy, lower alkyl substituted by halogen, lower alkoxy substituted by halogen, cyano, amino, di-lower alkyl amino or morpholinyl;
- $R^2$ is —$(CH_2)_n$-aryl, or —$(CH_2)_n$-heteroaryl wherein the aryl or heteroaryl groups are substituted by one or more substituents selected from the group consisting of halogen, lower alkyl, cyano, and lower alkoxy,
- $R^3$ is hydrogen or lower alkyl;

$R^4$ is aryl or heteroaryl, wherein aryl and heteroaryl are optionally substituted by one or more substituents selected from the group consisting of halogen, lower alkyl substituted by halogen, lower alkoxy substituted by halogen, and lower alkyl;

X is a bond or —$OCH_2$—; and n is 0, 1 or 2;

or a pharmaceutically acceptable acid addition salt thereof and a pharmaceutically acceptable carrier.

\* \* \* \* \*